(12) United States Patent
Gerrans et al.

(10) Patent No.: US 11,007,353 B2
(45) Date of Patent: *May 18, 2021

(54) FLUID SOURCE WITH PHYSIOLOGICAL FEEDBACK

(71) Applicant: Sanovas Intellectual Property, LLC, Reno, NV (US)

(72) Inventors: Lawrence J. Gerrans, San Anselmo, CA (US); Erhan H. Gunday, Great Neck, NY (US)

(73) Assignee: Sanovas Intellectual Property, LLC, Reno, NV (US)

( * ) Notice: Subject to any disclaimer, the term of this patent is extended or adjusted under 35 U.S.C. 154(b) by 194 days.

This patent is subject to a terminal disclaimer.

(21) Appl. No.: 16/006,264

(22) Filed: Jun. 12, 2018

(65) Prior Publication Data

US 2018/0289935 A1 Oct. 11, 2018

Related U.S. Application Data

(63) Continuation of application No. 14/311,949, filed on Jun. 23, 2014, now Pat. No. 9,993,627, which is a
(Continued)

(51) Int. Cl.
*A61M 25/10* (2013.01)
*A61B 17/22* (2006.01)
(Continued)

(52) U.S. Cl.
CPC . *A61M 25/10184* (2013.11); *A61B 17/22012* (2013.01); *A61B 17/22032* (2013.01);
(Continued)

(58) Field of Classification Search
CPC ............ A61M 25/10184; A61M 29/02; A61B 17/22012; A61B 17/22032;
(Continued)

(56) References Cited

U.S. PATENT DOCUMENTS 3,720,199 A 3/1973 Rishton et al.
4,186,745 A 2/1980 Lewis et al.
(Continued)

FOREIGN PATENT DOCUMENTS

EP 0894507 A2 2/1999
EP 1913882 A1 4/2008
(Continued)

OTHER PUBLICATIONS

Altinoz, et al.; "Noscapine and Diltiazem Augment Taxol and Radiation-Induced S-Phase Arrest and Clonogenic Death of C6 Glioma in Vitro"; May 2006; Surgical Neurology; 65(5):478-84.

*Primary Examiner* — Jason E Flick
(74) *Attorney, Agent, or Firm* — Forge IP, PLLC

(57) ABSTRACT

A balloon resection method is disclosed generally including inserting a catheter with at least one balloon having an outer wall with a resecting, non-slip surface for resecting unwanted biological material, such as tissues or tumors, and supplying fluid thereto in pulsed fashion to repeatedly deflate and inflate the balloon. In certain embodiments, a pump controls the pulsed supply of fluid based on an established frequency or change in volume. In some embodiments, the a keyed connector is used to identify the balloon type, and in some cases, intra-lumen diameters and densities are calculated. In some embodiments, the balloon portion of the catheter includes multiple balloon segments, which in some cases, are inflatable separately from one another.

20 Claims, 16 Drawing Sheets

Related U.S. Application Data continuation of application No. 13/548,890, filed on Jul. 13, 2012, now Pat. No. 8,790,299, which is a continuation of application No. 12/269,495, filed on Nov. 12, 2008, now Pat. No. 8,226,601.

(51) Int. Cl.
| | |
|---|---|
| *A61B 17/3207* | (2006.01) |
| *A61M 1/00* | (2006.01) |
| *A61M 29/02* | (2006.01) |
| *A61B 18/14* | (2006.01) |
| *A61B 17/32* | (2006.01) |
| *A61B 18/00* | (2006.01) |

(52) U.S. Cl.
CPC ..... *A61B 17/320725* (2013.01); *A61M 1/008* (2013.01); *A61M 29/02* (2013.01); *A61B 18/1492* (2013.01); *A61B 2017/22061* (2013.01); *A61B 2017/320004* (2013.01); *A61B 2018/00214* (2013.01); *A61B 2018/00898* (2013.01); *A61M 25/10188* (2013.11)

(58) Field of Classification Search
CPC ........ A61B 17/320725; A61B 18/1492; A61B 2017/22061; A61B 2017/320004; A61B 2018/00214; A61B 2018/00898
USPC ...................................................... 604/96.01
See application file for complete search history.

(56) References Cited

U.S. PATENT DOCUMENTS

| | | | |
|---|---|---|---|
| 4,423,725 A | 1/1984 | Baran et al. | |
| 4,446,867 A | 5/1984 | Leveen et al. | |
| 4,636,195 A | 1/1987 | Wolinsky | |
| 4,773,899 A | 9/1988 | Spears | |
| 4,824,436 A | 4/1989 | Wolinsky | |
| 4,921,484 A | 5/1990 | Hillstead | |
| 4,994,033 A | 2/1991 | Shockey et al. | |
| 5,049,132 A | 9/1991 | Shaffer et al. | |
| 5,100,425 A | 3/1992 | Fischell et al. | |
| 5,196,017 A | 3/1993 | Silva et al. | |
| 5,304,121 A | 4/1994 | Sahatjian | |
| 5,318,533 A * | 6/1994 | Adams | A61M 25/10182 128/903 |
| 5,336,234 A | 8/1994 | Vigil et al. | |
| 5,397,307 A | 3/1995 | Goodin | |
| 5,423,745 A | 6/1995 | Todd et al. | |
| 5,545,133 A | 8/1996 | Burns et al. | |
| 5,599,307 A | 2/1997 | Bacher et al. | |
| 5,611,775 A | 3/1997 | Machold et al. | |
| 5,647,847 A | 7/1997 | Lafontaine et al. | |
| 5,674,192 A | 10/1997 | Sahatjian et al. | |
| 5,707,352 A | 1/1998 | Sekins et al. | |
| 5,728,064 A | 3/1998 | Burns et al. | |
| 5,785,685 A | 7/1998 | Kugler et al. | |
| 5,833,644 A | 11/1998 | Zadno-Azizi et al. | |
| 5,868,708 A | 2/1999 | Hart et al. | |
| 5,873,852 A | 2/1999 | Vigil et al. | |
| 5,932,248 A | 8/1999 | Chen et al. | |
| 6,048,332 A | 4/2000 | Duffy et al. | |
| 6,129,705 A | 10/2000 | Grantz | |
| 6,149,596 A | 11/2000 | Bancroft | |
| 6,190,354 B1 | 2/2001 | Sell et al. | |
| 6,245,008 B1 * | 6/2001 | Leschinsky | A61M 1/106 600/18 |
| 6,248,092 B1 | 6/2001 | Miraki et al. | |
| 6,485,500 B1 | 11/2002 | Kokish et al. | |
| 6,544,221 B1 | 4/2003 | Kokish et al. | |
| 6,616,597 B2 | 9/2003 | Schock et al. | |
| 6,623,452 B2 | 9/2003 | Chien et al. | |
| 6,685,648 B2 | 2/2004 | Flaherty et al. | |
| 6,733,459 B1 | 5/2004 | Atsumi | |
| 7,014,652 B2 | 3/2006 | Cioanta et al. | |
| 7,025,718 B2 | 4/2006 | Williams | |
| 7,047,058 B1 | 5/2006 | Dvorsky et al. | |
| 7,462,165 B2 | 12/2008 | Ding et al. | |
| 7,569,032 B2 | 8/2009 | Naimark et al. | |
| 7,611,484 B2 | 11/2009 | Wellman et al. | |
| 7,658,966 B2 | 2/2010 | Kokish | |
| 7,727,226 B2 | 6/2010 | Chang et al. | |
| 8,052,668 B2 | 11/2011 | Sih | |
| 2002/0010418 A1 | 1/2002 | Lary et al. | |
| 2003/0114791 A1 | 6/2003 | Rosenthal et al. | |
| 2004/0059290 A1 | 3/2004 | Palasis | |
| 2004/0215140 A1 | 10/2004 | Forman | |
| 2005/0015049 A1 | 1/2005 | Rioux et al. | |
| 2006/0004323 A1 | 1/2006 | Chang et al. | |
| 2006/0047291 A1 | 3/2006 | Barry | |
| 2006/0135984 A1 | 6/2006 | Kramer et al. | |
| 2006/0189930 A1 | 8/2006 | Lary et al. | |
| 2007/0027075 A1 | 2/2007 | Smithrud | |
| 2007/0060942 A2 | 3/2007 | Zadno-Azizi | |
| 2007/0073264 A1 | 3/2007 | Stedman et al. | |
| 2007/0197963 A1 | 8/2007 | Griffiths et al. | |
| 2008/0039791 A1 | 2/2008 | Abboud et al. | |
| 2008/0051627 A1 | 2/2008 | Raju | |
| 2008/0171985 A1 | 7/2008 | Karakoca | |
| 2008/0208118 A1 | 8/2008 | Goldman | |
| 2008/0300571 A1 | 12/2008 | LePivert | |
| 2009/0229374 A1 | 9/2009 | Carlisle et al. | |
| 2010/0022943 A1 | 1/2010 | Mauch et al. | |
| 2010/0063534 A1 | 3/2010 | Kugler et al. | |
| 2010/0074895 A1 | 3/2010 | Petricoin, III et al. | |
| 2010/0113939 A1 * | 5/2010 | Mashimo | A61B 5/1076 600/470 |
| 2010/0121270 A1 | 5/2010 | Gunday et al. | |
| 2010/0145398 A1 | 6/2010 | Li et al. | |
| 2010/0280451 A1 | 11/2010 | Teeslink et al. | |
| 2010/0286467 A1 * | 11/2010 | Pesach | A61M 5/158 600/9 |
| 2011/0082427 A1 | 4/2011 | Golzarian et al. | |
| 2011/0293629 A1 | 12/2011 | Bastid et al. | |

FOREIGN PATENT DOCUMENTS

| | | |
|---|---|---|
| WO | 9103207 A1 | 3/1991 |
| WO | 9304727 A1 | 3/1993 |
| WO | 2006130326 A2 | 12/2006 |
| WO | 2009046206 A1 | 4/2009 |
| WO | 2009086269 A2 | 7/2009 |

* cited by examiner

FLUID SOURCE WITH PHYSIOLOGICAL FEEDBACK

FIELD OF THE INVENTION

The present invention relates to systems and methods for the resection of unwanted biological material, such as tissue growths and tumors, in bodily cavities. More specifically, the invention relates to a balloon catheter with a resecting surface that is operated in a pulsing fashion to resect the target material with minimal trauma.

BACKGROUND OF THE INVENTION

The removal of unwanted and/or life threatening biological material from interior portions of bodily cavities, such as organs, vessels, articular joints and structures, sinuses, and various bodily lumens, is a very common procedure in various medical specialties and disciplines, such as pulmonology, cardiology, urology, gynecology, gastro-enterology, neurology, otolaryngology, orthopedics, and general surgery. Accordingly, various instruments and methods have been employed to perform these procedures, which are generally well known in the art.

One of the most important complications in such procedures is bleeding. The bleeding and resulting morbidity of tissue that occurs in many of the currently known surgical procedures is the result of abrasive, traumatic, and invasive excising and removal techniques. Many of these techniques risk perforation of the vessel or lumen in which the procedure is being performed, resulting in grave complications for the surgeon and patient. In addition, many patient maladies are simply not remedied by these procedures because no interventional, minimally invasive treatment modality exists, the methods are not efficient, safe, and reproducible, and/or the instruments employed lack the appropriate visualization, physiological measurement, and/or feedback necessary to ensure the safety, efficacy, and reproducibility of the procedure. Accordingly, a new type of treatment is required.

One instrument that is commonly used in various types of medical procedures is an inflatable balloon catheter, of which many different types exist, which are utilized to perform various necessary functions. For example, these inflatable balloons are often used to control or stop bleeding, to hold instruments in place, or to prevent or facilitate other flow or movement within the bodily cavity. For example, many urological catheters are held in place via a balloon that impacts the sidewalls of the urinary tract, many gynecological instruments are held in place via balloons that impact the sidewalls of the vaginal vault, endovascular balloons are often used to control bleeding, inflatable balloons are sometimes used to control the backflow of radio-opaque agents injected into the cystic duct to detect the presence of gall stones during general surgical cholecystectomy procedures, and, recently, balloon catheters have been employed to release sinus congestion.

One particular application of such catheters is lung cancer. Among all types of cancer, this form is among the deadliest, as more than one third of all deaths due to cancer are caused by lung cancer. Over 1.5 million new cases are diagnosed worldwide each year. The most frequent cause of death for lung cancer patients is airway obstruction. In lung cancer patients, one third of all cases initially, and another third of the cases in the long term, present main airway obstruction, which may cause asphyxia, hemorrhaging, and infection. These complications are the most frequent causes of death in lung cancer patients.

Use of interventional bronchoscopy for the treatment of lung cancer and the resultant airway obstruction increases the quality of life and survival rates of patients suffering from Chronic Obstructive Pulmonary Disease (COPD) and the obstructive co-morbidities associated with the cancer. Accordingly, balloon catheters have been routinely used with various endoscopes and with flexible and rigid bronchoscopes for dilation, as a tamponade to stop bleeding, and as an interference fixation device to hold instruments in place and prevent the retropulsion of those instruments under backflow pressure.

In light of the aforementioned need for a new type of treatment for removing undesirable biological material in bodily cavities, it has been realized that inflatable balloon catheters may further be employed as interventional tools for the excision and removal of such materials—such as endoluminal obstructions and tumors and endovascular occlusions—in various applications, such as the aforementioned interventional medical specialties of pulmonology, cardiology, urology, gynecology, gastro-enterology, neurology, otolaryngology, and general surgery. The use of balloon catheters in this way has presented a method of treatment that is simple, safe, highly effective, and inexpensive compared to other types of methods and devices that are used, such as mechanical, laser, electrocautery, cryotherapy, etc.

Accordingly, a new class of balloons has been suggested for this purpose, such as that disclosed in European Patent Application No. EP 1 913 882 by Karakoca. This device employs a balloon catheter with a hardening surface, which can be inserted into bodily cavities. After the device is inserted, the balloon is inflated, and the balloon is moved back and forth within the cavity such that the textured surface performs a shaving action on the unwanted biological material. In this way, the targeted material is resected.

However, this particular instrument and method of using it suffers from a number of disadvantages and shortcomings. One of the most significant problems with this resector balloon is that unwanted biological material is removed by shaving it with the hardened surface on the outside of the balloon—i.e., by moving the balloon back and forth and/or rotating it. This mechanism of action can be abrasive and traumatic. Moreover, the hardened surface coupled with the shaving action can sometimes lack the precision necessary to prevent complications such as bleeding and structural perforation of the affected anatomical structure. Furthermore, the amount of torque and back and forth force needed on the balloon may cause a device failure, particularly where the balloon is attached to the catheter.

Another disadvantage of this resector balloon is that its hardened surface is a separate membrane located on the outside of the balloon. This membrane has different stretching characteristics than the balloon and effects the performance of the balloon catheter negatively. It may be required to pre-exercise the balloon catheter outside the body before use. Additionally, it may break off under the frictional stresses of the procedure and further obstruct or compromise the bodily cavity in which the balloon is deployed.

Another problem with this resector balloon is that it further lacks accuracy because it lacks the capability to precisely gauge the size of the environment in which it is being used to provide physiological measurements and feedback that could aid treatment intervention and efficacy. For example, there is no way for the surgeon to know the diameter of the affected bodily cavity itself, proximal or distal to the obstruction therein. Similarly, there is no way for the surgeon to know the intra-lumen diameter where the unwanted tissue growth or tumor resides, and further, no way to accurately adjust for changes in this diameter over time as the growth or tumor is resected. Because it has no mechanism for measuring the intra-lumen diameter at different points within the cavity, and particularly, how this changes over time, one is not able to be properly adjust the amount of pressure supplied to the balloon and thereby prevent complications and expedite treatment.

A related problem with this device is that there is no way for a physician to measure the intra-articular space between two articular structures, endplates, or surfaces.

Yet another related problem with this device is that there is no way for the surgeon to know the density of the bodily cavity proximal or distal to the obstruction, nor can the surgeon know the density of the growth or tumor itself. Because there is no mechanism for measuring the density of the cavity or the obstruction, one is likewise unable to properly control the pressure in the balloon to aid surgical precision, minimize potential complications, and expedite the procedure.

Still another related problem with this device is that it does not have a way of identifying the type of balloon catheter that is connected to the pump. As a result, the balloon may be accidentally over-inflated, and thus, the balloon could burst.

Another disadvantage of this resector balloon is that it is comprised of a single, unitary structure, which means that one is only able to inflate the entire balloon as a whole. This results in several deficiencies, including: the inability to measure the intra-lumen diameter at different locations, including both the bodily cavity itself (proximal/distal to obstruction) and the obstructive biological material; the inability to pinpoint the location(s) requiring the maximum pressure in order to precisely and methodically resect the obstruction; the inability to tamponade specific areas in order to control bleeding; the inability to capture material that has been excised in order to extract it from the bodily cavity; and a tendency for the balloon to slip and migrate.

Yet another deficiency of this device is that it is not able to be positioned as optimally as may be desired. For example, the overall diameter of this balloon catheter requires a rigid or flexible endoscope with a working channel. In addition to the fact that such endoscopes may not be readily available, they are single lumen devices. As a result, a guide wire cannot be used to guide them into bodily cavities either through a rigid or flexible endoscope or alongside, in parallel to, a rigid or flexible endoscope. Likewise, this device does not have the ability to linearly translate the balloon along the catheter construct, which would enable one to optimize balloon placement and productivity. Finally, the device does not include material for externally identifying its position, such as a radio-opaque material. Therefore, one is not able to easily identify the position of the balloon via an external imaging modality, such as radiographic or ultrasonic imaging. Each of these shortcomings contributes to one's inability to position the balloon as precisely as may be desired.

Another disadvantage of this resector balloon is that there is no way to provide the physician illuminated light, non-thermal illuminated light, and direct visual feedback of the area ahead of the balloon, ahead of the balloon looking back towards the balloon, along the sides of the balloon or behind the balloon to optimize treatment intervention and efficacy.

A further deficiency of this resector balloon stems from the fact that it is a single lumen device where the proximal end is closed off. As a result, it does not allow for passage of fluid, such as air or blood, from the distal end of the catheter to the proximal end when the balloon is inflated. This is particularly important in interventional pulmonology applications, where aspiration in the event of airway obstruction is critical. Likewise, this is important in interventional cardiology applications to permit the bypass of blood flow during the operation of a vessel segment.

Another deficiency of this device is that it does not have the ability to deliver cryogenic agents or forms of energy that could assist in the resection of the undesirable biological material. As a result, one is unable to supply cryogenic agents or forms of energy such as radio-frequency, ultrasonic, and electrosurgical energy in order to perform ablation, desiccation, cauterization, excision, decortications, and/or tissue modification in order to optimize hemostasis and resection.

A further deficiency of these balloon catheters is that there is no way to provide localized delivery of drugs, stents, biologic materials, nano-particulates, or related technologies to the surface of the balloon. Thus, one is unable to use the device to supply these means of providing medicinal, therapeutic, and restorative treatments.

What is desired, therefore, is a resector balloon system for removing undesirable biological materials that does not cause unnecessary trauma to the affected bodily cavity as a result of a shaving action used to resect that material. What is also desired is a resector balloon system with controllable rates of inflation and deflation. What is further desired is a resector balloon system that does not require a separate membrane affixed to the exterior of the balloon. What is also desired is a resector balloon system that can be administered either through an endoscope, alongside an endoscope, or via radiographic or ultrasonic imaging. What is also desired is a resector balloon system that is able to provide physiologic feedback to determine intra-lumen diameters and densities where the unwanted biological material resides and at locations proximal or distal to such material, the intra-articular space between two articular structures, and the type of balloon catheter connected. What is also desired is a resector balloon system that is able to provide dimensional and performance metrics of the balloon catheter construct in vivo. What is further desired is a resector balloon system that can be optimally positioned within the bodily cavity and can pinpoint specific areas at which to provide maximum inflation. What is also desired is a resector balloon system that can supply light and visualization capabilities, cryogenic agents and various forms of energy to assist surgical techniques, and drugs and related materials to the anatomical site. What is further desired is a resector balloon system that allows for the passage of fluids from the proximal to the distal end of the catheter.

SUMMARY OF THE INVENTION

Accordingly, it is an object of the present invention to provide a resector balloon system for removing undesirable biological material that does not require a shaving mechanism of action.

It is a further object of the present invention to provide a resector balloon system for removing undesirable biological material that does not employ a separate membrane affixed to the outside of the balloon.

It is yet another object of the present invention to provide a resector balloon system for removing undesirable biological material that provides physiological feedback from which the intra-lumen diameter where the material resides, as well as the bodily cavity itself proximal and distal to the material, can be determined, and the pressure and flow supplied to the balloon can be adjusted accordingly.

It is still another object of the present invention to provide a resector balloon system for removing undesirable biological material that provides physiological feedback from which the intra-articular space between two articular structures, endplates, or surfaces can be determined, and the pressure and flow supplied to the balloon can be adjusted accordingly.

It is yet another object of the present invention to provide a resector balloon system for removing undesirable biological material that provides physiological feedback from which the intra-lumen density where the material resides, as well as the bodily cavity itself proximal and distal to the material, can be determined, and the pressure and flow supplied to the balloon can be adjusted accordingly.

It is another object of the present invention to provide a resector balloon system for removing undesirable biological material that can identify the type of balloon catheter that is connected to the pump.

It is still another object of the present invention to provide a resector balloon system for removing undesirable biological material where the balloon portion has different segments that can be inflated independently.

It is yet another object of the present invention to provide a resector balloon system for removing undesirable biological material that has at least one additional passageway other than that used for the fluid that inflates the balloon.

It is another object of the present invention to provide a resector balloon system for removing undesirable biological material that enables the balloon to be translated along the catheter.

It is still another object of the present invention to provide a resector balloon system for removing undesirable biological material that facilitates exterior imaging.

It is yet another object of the present invention to provide a resector balloon system for removing undesirable biological material that provides visualization from within the bodily cavity.

It is another object of the present invention to provide a resector balloon system for removing undesirable biological material that can deliver energy to the target area.

It is yet another object of the present invention to provide a resector balloon system for removing undesirable biological material that can deliver cryogenic agents to the target area.

It is still another object of the present invention to provide a resector balloon system for removing undesirable biological material that can deliver drugs, stents, nano-particulates, and similar materials to the target area.

In order to overcome the deficiencies of the prior art and to achieve at least some of the objects and advantages listed, the invention comprises a method of resecting biological material with a resector balloon system, the method including inserting a catheter comprising at least one balloon having an outer wall with a resecting surface into a bodily cavity having biological material to be resected, inflating the balloon by supplying fluid thereto such that the resecting surface of the balloon contacts the biological material, and repeatedly deflating and inflating the balloon by supplying fluid to the balloon in pulsed fashion such that the repeated deflation and inflation causes the resecting surface to resect the biological material.

In some of these embodiments, the step of inflating the balloon includes supplying fluid to the balloon with an electro-pneumatic pump, and the step of repeatedly deflating and inflating the balloon is controlled by the electro-pneumatic pump based at least partially on an established volume change or frequency. In some cases, the method further includes detecting a balloon type for the catheter inserted into the bodily cavity, wherein the step of inflating the balloon is controlled based at least partially on the balloon type detected, and in certain cases, the step of repeatedly deflating and inflating the balloon includes determining a density of the biological material or a diameter within the biological cavity, and adjusting the amount of fluid supplied to the balloon based at least in part on the determined density or diameter.

In some embodiments, the at least one balloon includes a plurality of balloon segments, and the step of inflating the balloon includes inflating at least one of the balloon segments separately from at least one other balloon segment.

The invention also comprises a resector balloon system, including a catheter with at least one balloon having an outer wall, the outer wall comprising a resecting surface for resecting biological material, and a pump that inflates the balloon by supplying fluid thereto, wherein the pump supplies fluid to the at least one balloon in pulsed fashion to repeatedly deflate and inflate the balloon.

In some embodiments, In certain advantageous embodiments, the pump is an electro-pneumatic pump. In some embodiments, the pump includes a processor that controls the pulsed supply of fluid based on an established frequency, while in other embodiments, the pump includes a processor that controls the pulsed supply of fluid based on an established change of volume within the balloon.

In some embodiments, the invention further includes a connector that connects the catheter to the pump, wherein the connector is a balloon identification connector with which the pump identifies the balloon. In some of these embodiments, the connector includes a balloon identification plate and a key that orients the identification plate when the catheter is connected to the pump such that the pump identifies the balloon using the identification plate. In some cases, the pump identifies the balloon from the identification plate electro-optically, while in other cases, the pump identifies the balloon from the identification plate electro-mechanically. In certain embodiments, the pump includes balloon profile data corresponding to the balloon and a processor that controls the supply of fluid to the balloon based at least partially on the balloon profile data. The balloon profile data may also include correction data for different types of tissues.

In some embodiments, the pump includes at least one sensor for making at least one measurement, and a processor that calculates a density of the biological material in the biological cavity based at least partially on the at least one measurement and the balloon profile data. In some of these embodiments, the at least one sensor includes a sensor that determines the pressure of the fluid output to the balloon and a sensor that determines the flow of the fluid output to the balloon, and in some cases, the pump controls the supply of fluid to the balloon at least partially based on the calculated density.

Similarly, in some embodiments, the pump includes at least one sensor for making at least one measurement, and a processor that calculates a diameter in the biological cavity based at least partially on the at least one measurement and the balloon profile data. In some of these embodiments, the at least one sensor includes a sensor that determines the pressure of the fluid output to the balloon and a sensor that determines the flow of the fluid output to the balloon, and in some cases, the pump controls the supply of fluid to the balloon at least partially based on the calculated diameter.

In certain embodiments, the system further includes a connector that connects the catheter to the pump, wherein the connector is a balloon identification connector with which the pump identifies the balloon, the pump includes balloon profile data corresponding to the balloon the pump includes a processor that determines a desired frequency or change in volume in the balloon based at least partially on the balloon profile data, and the pump controls the supply of fluid to the balloon based at least partially on the determined frequency or change in volume.

In some embodiments, the at least one balloon comprises a plurality of balloon segments and the catheter includes a plurality of lumens through which the pump supplies fluid to the balloon segments such that the pump inflates at least one of the balloon segments separately from at least one other of the balloon segments.

In certain advantageous embodiments, the system further includes at least one outer lumen for supplying fluid to the at least one balloon segment and an inner lumen. In some of these embodiments, the inner lumen comprises an air or bodily fluid passage, while in some embodiments, at least one guide wire is disposed in the inner lumen. In certain of these embodiments, the system further includes at least one channel connecting the inner lumen and the outer surface of the balloon for delivering a medicinal or therapeutic agent to the biological cavity. In some of these embodiments, the catheter includes an imaging device aperture, further comprising a fiber optic bundle disposed in the catheter and exiting the hole for viewing the biological cavity. Some of the lumens can be used for multiple purposes. For example, once the catheter is inserted into position with the aid of the guide wire, the inner lumen can then be used for visualization.

In certain embodiments, the pump includes a vacuum source with which the pump evacuates resected material from the bodily cavity, through a channel in the inner lumen. In some embodiments, the pump includes a vacuum source that evacuates the fluid from the balloon.

In some embodiments, the system further includes an energy source for supplying energy and at least one wire molded into the catheter for conducting energy from the energy source to the biological cavity.

In certain advantageous embodiments, the fluid is a gas. In some embodiments, the fluid is a cryogenic fluid.

In certain advantageous embodiments, the system includes a mesh molded into the catheter, wherein the resecting surface comprises a textured surface of the outer wall of the balloon produced by the mesh. In other embodiments, the outer wall of the balloon comprises a plurality of inflatable cavities that provide the resecting surface. In still other embodiments, the system further includes a plurality of spring wires mounted to the outer wall of the balloon, wherein the resecting surface comprises the spring wires, and in some cases, the system also includes an energy source connected to the spring wires for supplying energy thereto.

In some embodiments, the balloon has first and second ends, and the system further includes at least one imaging marker mounted adjacent at least one of the ends of the balloon, which in some cases, comprises a radio-opaque ring.

DETAILED DESCRIPTION OF THE INVENTION

Figure 1:
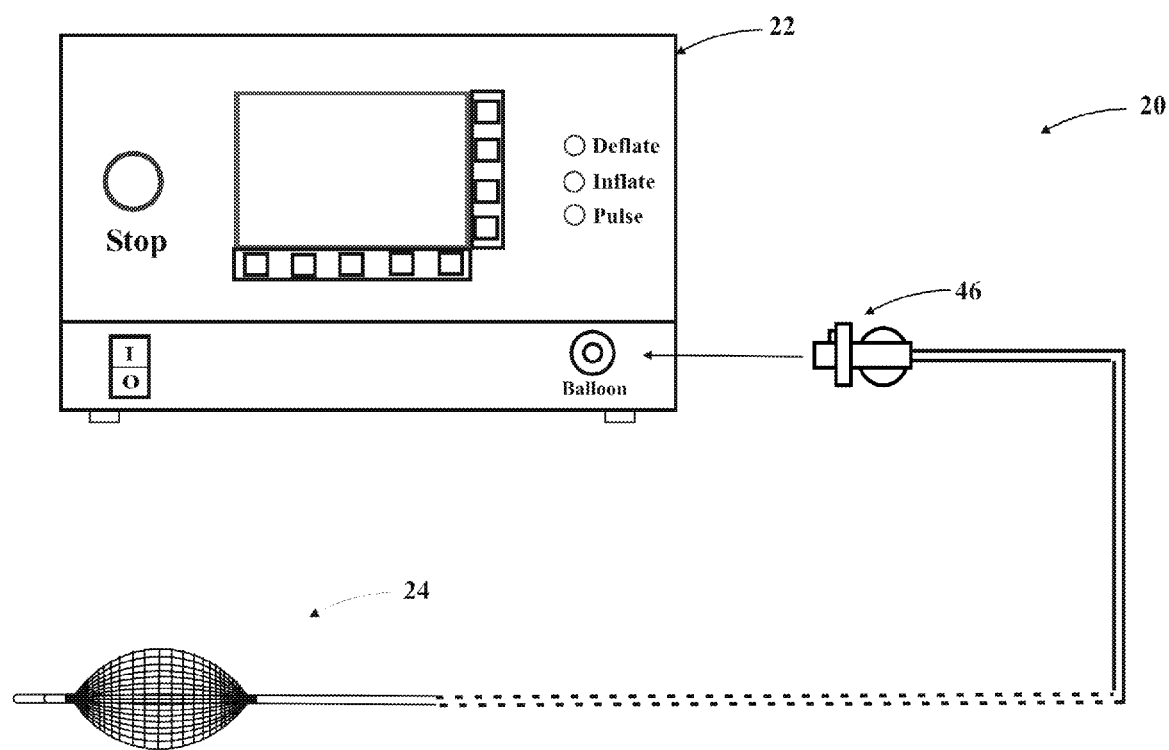
FIG. 1 is a front, partially schematic view of a resector balloon system in accordance with the invention.

The basic components of one embodiment of a resector balloon system in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The system 20 includes a fluid source (22), such as an electro-pneumatic pump having controls on the front thereof, from which a physician or assistant can control the system (as well as a remote control unit), which is further described below. A balloon catheter (24) is connected to the pump (22), to which the pump (22) supplies a fluid, such as a gas, liquid, or mixture thereof. In certain cases, a cryogenic fluid is supplied by the pump (22) in order to further aid a particular procedure, such as tumor desiccation.

Figure 2A:
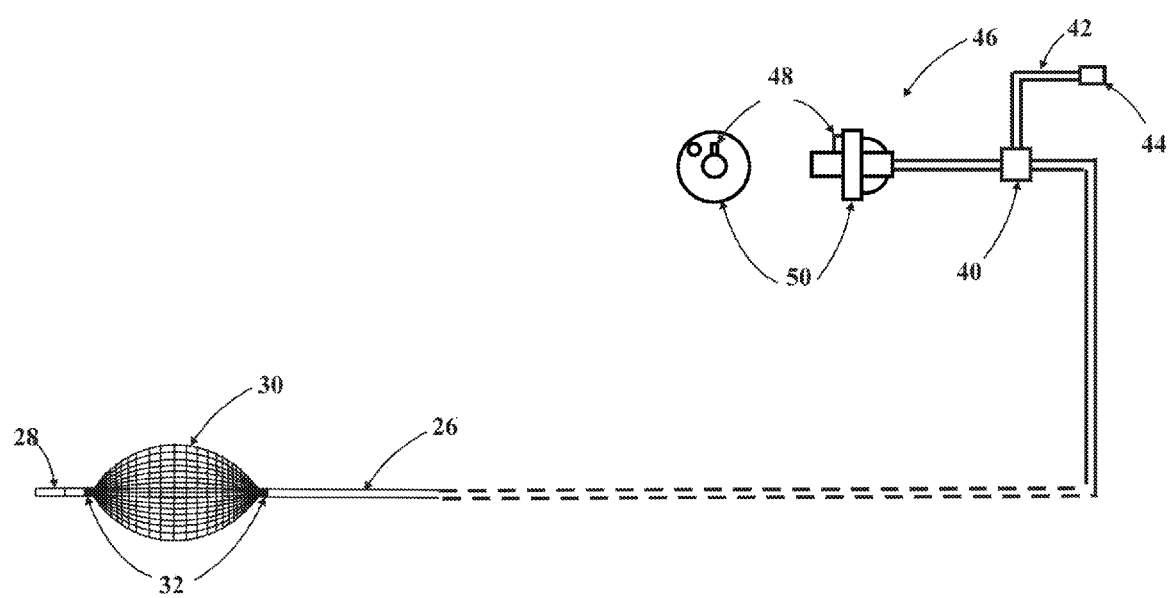
FIG. 2A is a front, partially schematic view of the balloon catheter of the system of FIG. 1.
Figure 2B:
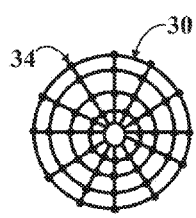
FIG. 2B is an end, partially cross-sectional view of the inflated balloon of the system of FIG. 2A.

As shown in FIGS. 2A-B, the balloon catheter (24) includes a catheter (26) made of a polyethylene material and having an outer diameter of 1.8 mm and a length of about 1.2 to 3 meters. A bendable section (28) having a length of about 5 to 10 mm at the distal end of the catheter (24) serves as a safety tip. As a result, when the catheter (24) is inserted through the available opening of a bodily cavity, it will bend instead of puncturing the walls of the cavity.

A balloon portion (30) made of latex or other suitable material is located near the distal end of the catheter (24) or at an otherwise desirable, predefined distance along the catheter (24). The balloon (30) comes in a variety of sizes and diameters, which can be selected to suit the particular application for which the device is being used. Typically, such balloons will have lengths of 5, 10, 15, 20, 30 or 50 mm and diameters of 2.5, 5, 10, 15, 20, 30 or 50 mm. This variety of available balloon sizes allows the balloon catheter (24) to be used in bodily cavities of various diameters and dimensions, such as large and small bronchial branches, sinuses, and vessels, having different types of tumors and tissues to be treated. The pump (22) supplies the air at a pressure of approximately 2 atmospheres in order to be able to inflate such balloons to full size, ranging from 2.5 mml to 50 mml.

In certain advantageous embodiments, the balloon (30) includes imaging markers (32), such as radio opaque rings, located at or near the ends thereof. Such markers can be selected and appropriately positioned in order to reflect the relevant waves of various imaging modalities (e.g., x-ray) in order to allow the use of such modalities to assist with the precise positioning of the balloon (30).

Referring to FIG. 2B, which shows a cross-section of the balloon (30), the balloon is covered with a flexible resecting surface (34), which may, for example, comprise a fiber mesh affixed to the surface of the balloon (30). In certain advantageous embodiments, the resecting surface (34) comprises a textured surface approximately 0.2 mm thick that is an integral part of the balloon and which is incorporated therein during the molding process. In these cases, the resecting surface (34) is made by integrating into the balloon material a fine, fiber mesh, which can be made of lycra, polyurethane, composite springs, or other appropriate material. The crossover point of the mesh members produce outwardly-facing, small knots or dimples, which create micro-impacts on the tumor tissue (or other biological material to be resected) during the inflation/deflation cycles further described below. In other embodiments, dimensional surface structures or inflatable sinuses that are encapsulated in the surface substrate of the balloon (30) are employed. Such impregnated structures within the surface substrate of the balloon can mimic mesh-like structures, bumps, ridges, etc.

Referring back to FIG. 2A, the balloon catheter (24) includes an inner lumen breakout Y junction (40) to facilitate the introduction of a guide wire, air bypass, drug delivery, or visualization conduit. The proximal end of the inner lumen (42) after Y junction (40) is terminated with a luer connector (44). The outer lumens are terminated at their proximal end with a keyed connector (46), which includes a key (48) and a balloon identification plate (50).

The Y junction (40) serves several purposes. First, it brings out a separate, inner lumen (42) of the catheter (24) to a suitable connector, such as the aforementioned luer connector (44), in order to provide an independent passage, such as a two-way air passage between the distal and proximal ends of the balloon catheter (24), which can be critical in certain applications (i.e., bronchoscopy) when the balloon is inflated. Additionally, the Y junction (40) also includes a shut-off valve (not shown) for stopping the balloon (30) from deflating. This may be used, for example, when it is required to leave the inflated balloon in place for a lengthy period of time in order to treat chronic bleeding.

As noted above, the catheter (24) is terminated at the proximal end with a keyed balloon identification plate (50). The purpose of this connector is to electronically detect the catheter (24) when it is inserted into the pump (22) and to identify the particular type of balloon catheter being used. The key (48) orients the connector (46) and the identification plate (50) in such a way that the balloon type can be identified by the pump (22) using electro-optical or electromechanical means.

Each type of balloon (30) that can be used with the pump (22) is characterized, and balloon profile data is registered in lookup tables. By identifying the type of balloon (30) that is connected the pump (22), the appropriate profile data can be retrieved and used to ensure that the appropriate pressure, volume, flow, and timing adjustments can be made to safely and effectively operate the balloon (30). The balloon profile data contained in the lookup table, along with appropriate pressure and flow measurements (as further discussed below), allows one to make tissue density approximations. This balloon profile data and approximated lumen diameter and tissue density, as well as any user commands, are used to adjust the amount of gas the pump (22) delivers to the balloon (30) in order to achieve the desired inflation and deflation amounts.

Figure 2C:
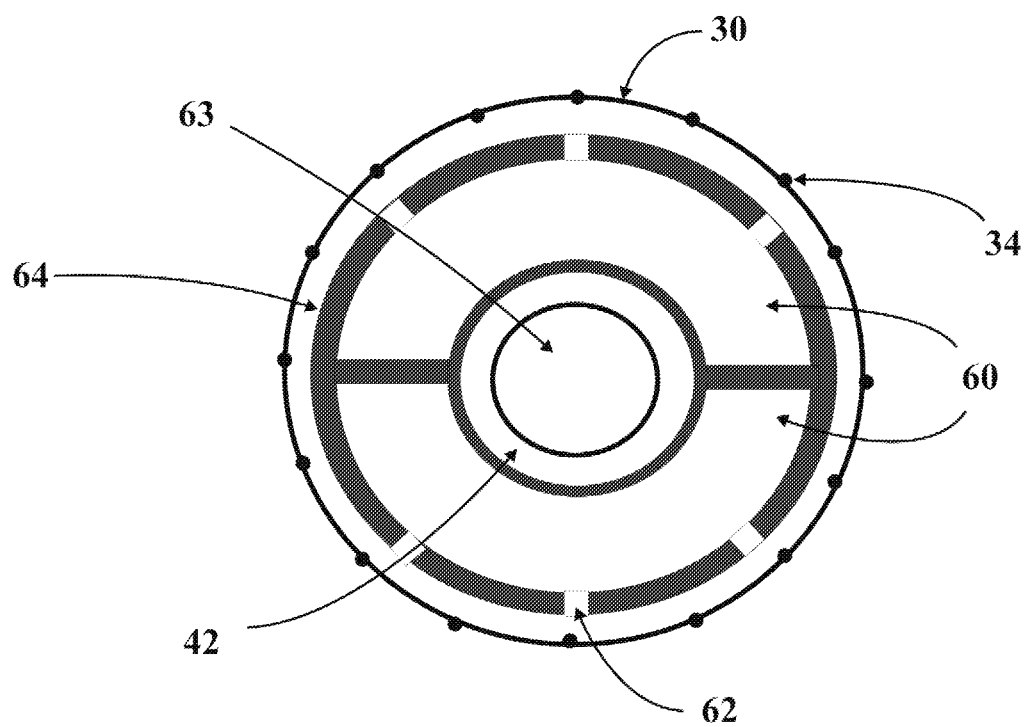
FIG. 2C is a partially cross-sectional view of the deflated balloon of the system of FIG. 2A.

As shown in FIG. 2C, which shows a cross-section of the catheter (26) at the distal end where the deflated balloon (30) with the resecting surface (34) is located. In certain embodiments, the inner lumen (42) of the catheter (26) extends through the bendable section of the catheter tip (28) and is open at the distal end. As noted above, in certain applications, such as bronchoscopy, this inner lumen (42) serves as a passageway that allows the air to move freely in both directions from each end of the balloon (30) when it is inflated. Additionally, the inner lumen (42) can be used as a means for accurately positioning the balloon catheter (24), as it can be used as a conduit for a guide wire (63) when inserting the deflated balloon catheter (24) into the bodily cavity. In other applications, such as in treating coronary artery disease, bypass holes (not shown) to the inner lumen may be provided at an appropriate location after the proximal end of the balloon (30) and the inner lumen (42) is thereafter blocked such that a breakout junction therefor is unnecessary.

The outer lumens (60) of the catheter (26) are used to inflate and deflate the balloon (30) through the holes (62) provided in the catheter's outer walls (64). These outer lumens (60) are blocked at the distal end of the balloon (30) so that air intended for inflation and deflation will not escape.

Figure 3A:
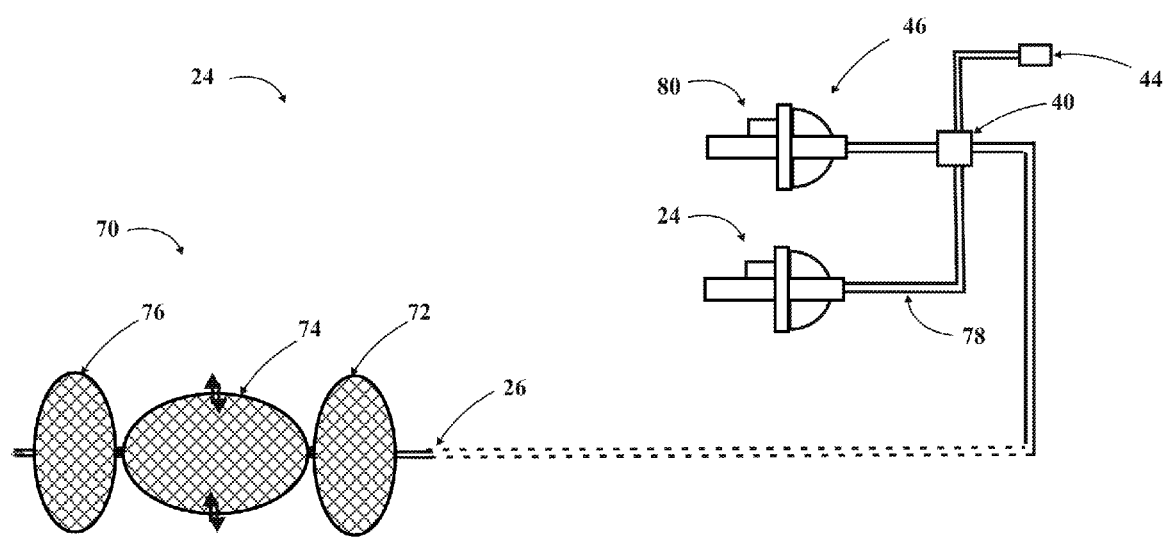
FIG. 3A is a front, partially schematic view of the balloon catheter of FIG. 2A employing multiple balloon segments.
Figure 3B:
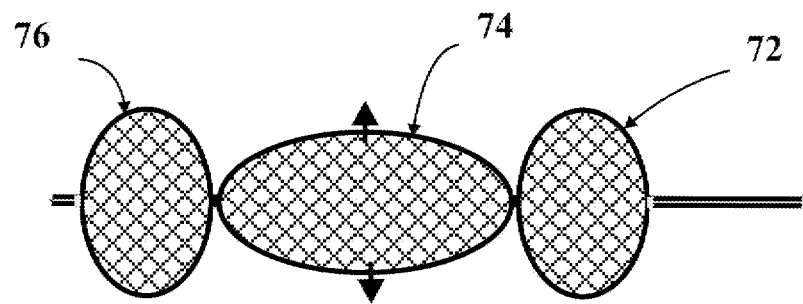
FIG. 3B is a side view of the balloon of the catheter of FIG. 3A with the center balloon inflated.

In certain advantageous embodiments, as illustrated in FIGS. 3A-B, the balloon catheter (24) includes a multi-balloon construct (70) at its distal end. This construct may include, for example, a proximal balloon segment (72), a center balloon segment (74), and a distal balloon segment (76). At the proximal end of the catheter (24), the Y junction (40) brings out another lumen (78) that supplies fluid to the proximal balloon segment (72) and the distal balloon segment (76) separately from the center balloon segment (74). The additional lumen (78) is connected to another keyed connector (80), similar to the keyed connected (46). In this way, the center balloon segment (74) is inflated and deflated independently of the proximal and distal balloons (72,76).

Figure 3C:
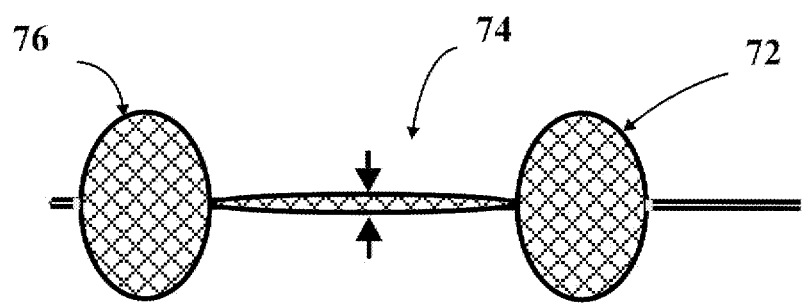
FIG. 3C is a side view of the balloon of the catheter of FIG. 3A with the center balloon deflated.

Employing separate proximal and distal balloon segments in this way serves several purposes. First, one is able to inflate the proximal and distal balloon segments (72,76) to an amount appropriate to hold the catheter (24) steady where the tissue to be removed is located while the center balloon (74) is cyclically inflated and deflated to resect the unwanted biological material, as illustrated in FIGS. 3B-C. By doing so, one can prevent the balloon (30) from slipping and migrating during the procedure, and possibly causing damage to the bodily cavity itself, which is particularly important in cavities subject to significant backflow pressures and in applications where balloon catheterization is required for an extended period of time. Additionally, by inflating the proximal and distal balloons (72,76), one can prevent the resected material from escaping into the bodily cavity, and instead, can capture the loose tissue for easy removal. Finally, by employing multiple, independently inflatable bladders or sinuses in this way, one is able to more selectively and precisely tamponade different sections of the bodily cavity, measure their intra-lumen diameters and densities, and resect obstructive tissue.

Figure 3D:
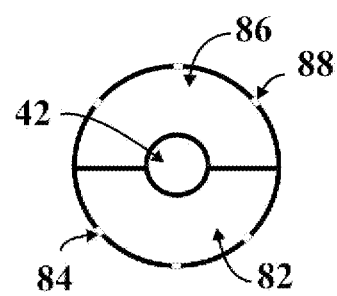
FIG. 3D is a partially cross-sectional view of the balloon catheter of FIG. 3A.

FIG. 3D shows how the outer lumens are used to inflate and deflate the three balloons (72, 74, 76). As noted above, the inner lumen (42) is used for air bypass and/or a guide wire conduit. The lower lumen (82) has inflation/deflation hole (84) in the catheter walls only at the position along the length of the catheter (24) where the center balloon (74) is located, while the upper lumen (86) contains inflation/deflation holes (88) only at the position along the length of the catheter where the proximal and distal balloons (72,76) are located. It should be noted that the proximal and distal balloon segments (72,76) can also be inflated/deflated independently from each other by further separating the outer lumen to include an additional lumen, and positioning the inflation/deflation holes at the appropriate locations along the length of catheter (24). Likewise, additional balloon segments could be added, which could each similarly be inflated independently from the others by increasing the number of lumens and adding a separate termination at the proximal end at the Y junction (40).

Figure 3E:
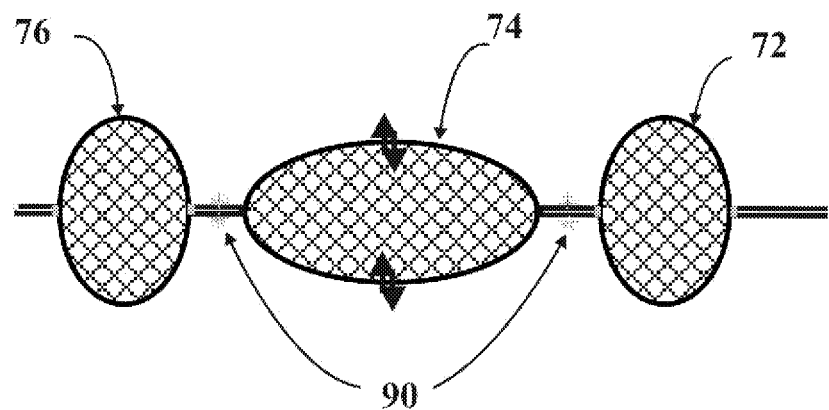
FIG. 3E is a side view of the balloon of the catheter of FIG. 3A with the balloon segments spatially separated.

Though the balloon segments illustrated in FIGS. 3A-C are shown adjacent one another, in other embodiments, as shown in FIG. 3E, the different balloon segments may be spatially separated from each other. The balloon segments may be separated by, for example, a distance of about 1 cm, though this separation can be more or less depending on the particular application. By separating the balloon segments in this way, holes (90) can be provided to other lumens (92) in the catheter.

Figure 3F:
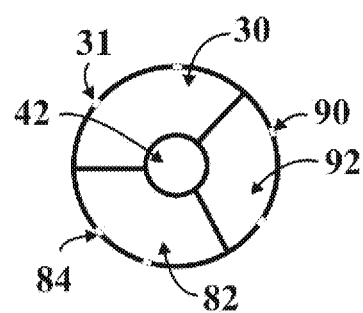
FIG. 3F is a partially cross-sectional view of the balloon catheter of FIG. 3E.

As shown in FIG. 3F, the lumens (92) and holes (90) can be used to deliver, for example, a medicinal drug. In this way, with the proximal and distal balloons (72, 76) remaining inflated and the center balloon resecting the unwanted biological material (as further described below), the drug is contained in the targeted site and evenly distributed. It should be noted that, however, that in other embodiments, such drugs, nano-particulates, etc. may be dispersed through multiple distal tips or through orifices in the lateral walls of the balloon. Accordingly, such drugs can be released via a methodic and/or timed release.

The lumens (92) and holes (90) can be used to deliver any number of things to assist with opening the cavity, circulation, aspiration, respiration, assisting the decomposition of an obstruction, or stimulating healing in the affected area, including air, aspirates, drugs, biologics, biogenetic agents, nano-particulates, solutions, stem cell and gene therapies, and stents and scaffolds. Specifically, the device could be used for the deployment and implantation of pro-generative vehicles and/or catalysts in the repair, treatment, and therapy of the targeted areas, including biologic, nano-particulate materials and/or biogenetic materials, structures, scaffolds, and similar devices and vehicles, including, for example, bone morphogenetic proteins, microcrystalline nano-particulates, collagens, de-mineralized bone chips, calcium based structures, poly glycolic acids, poly lactic acids, and hyaluronic acids. The device can likewise be used for the deployment and implantation of inert, inelastic, and semi-rigid materials, such as, for example, PEEK, ceramic, cobalt chrome, titanium, and stainless steel, and for the implantation of reinforcing constructs within, along, and/or around anatomic structures, which may be deployed and then impregnated, impacted, and otherwise filled, either prior to or after insertion, with inert materials including, for example, polymethyl meth-acrylate, bone cements, polyethylene, polypropylene, latex, and PEEK.

Additionally, in some of these multiple-balloon embodiments, the above-described imaging markers (e.g., radio opaque rings), can be located at or near the ends of each balloon segment in order to facilitate the use of certain imaging modalities to assist with the precise positioning of the balloons.

Figure 4A:
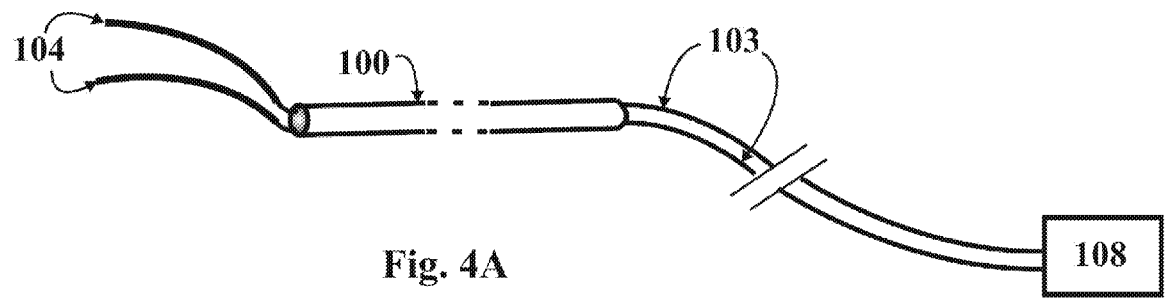
FIG. 4A is a side, partially schematic view of the balloon catheter of FIG. 1 with an energy delivery assembly.
Figure 4B:
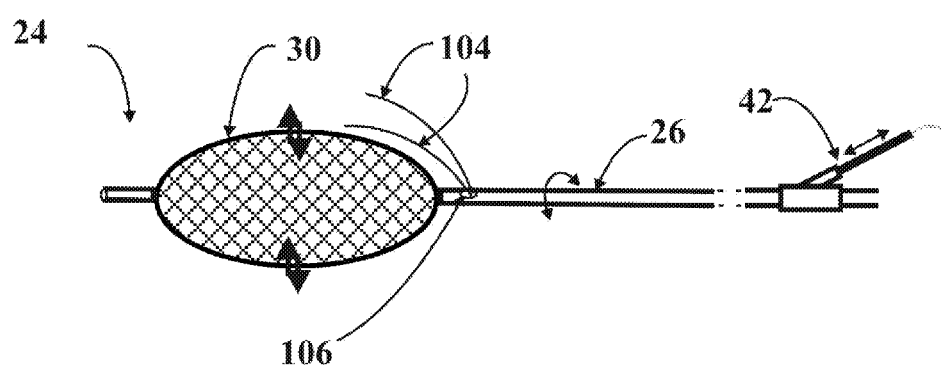
FIG. 4B is a side, partially schematic view of the balloon catheter of FIG. 4A.

As illustrated in FIG. 4A, in certain advantageous embodiments, a flexible catheter (100) with electrically conductive wires (103) and electrodes (104) is used to deliver energy to a desired biological material to be treated. As shown in FIG. 4B, an access hole (106) is used to introduce the electrocautery electrodes (104) to the target site. The electrodes (104) are molded into the flexible catheter (100), and are electrically connected to conductive wires (103), which are also molded into the catheter (100) and electrically insulated from one another. The distal ends of the wires (103) are, in turn, connected to an energy generating device for supplying the requisite energy (108), such as, for example, a suitable electrosurgical unit.

The electrodes (104) are made of suitable spring metals that are straight inside the lumen of the catheter (26), but spring into their original shape when pushed out through the access hole (106). The electrodes are deployed by pushing the catheter (100) in and out at the Y junction (40). The electrodes (104) are positioned in the desired position by rotating the balloon catheter (26) and incrementally inflating and deflating the balloon (30) as needed. It should be noted that both monopolar (one of the electrodes is remotely connected) and bipolar (both electrodes are localized) implementations may be employed. In this way, various forms and types of energy, such as radio-frequency and electrosurgical energy, can be supplied in a 360° fashion to perform ablation, cauterization, excision, decortications, and/or tissue modification in order to optimize hemostasis and resection. A similar energy delivery system can be constructed for delivery of ultrasound.

In certain advantageous embodiments, the invention also includes insulating materials and insulation barriers along and within the surfaces of the balloon construct to insulate the balloon from the thermal, ultrasonic, and associated deleterious effects of the different forms energy delivered by the above described balloon catheter (24). Accordingly, the balloon (30) is protected against becoming deflated or otherwise comprised under the stress of the energy delivery process(es).

Figure 5:
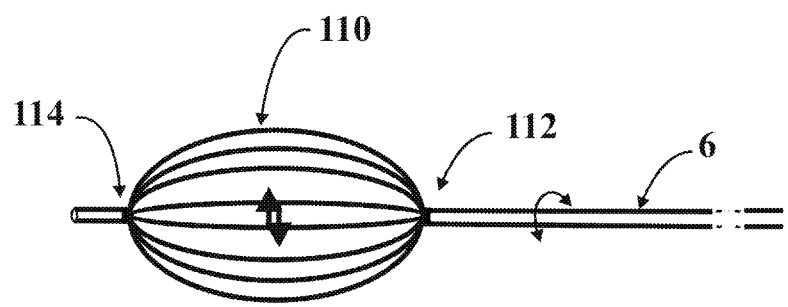
FIG. 5 is a side view of the balloon catheter of FIG. 1 with spring wires mounted to the balloon.

As illustrated in FIG. 5, in certain embodiments, straight, steel spring wires (110) are mounted on the balloon (30) in a cylindrical fashion. The wire ends are fixed to the balloon catheter (24) at the proximal end (112) of the balloon (30)

such that they do not move with respect to the catheter (26). At the distal end (114), the wires (110) are not fixed and extend far into channels that are provided in the balloon catheter (26). Accordingly, when the balloon (30) is inflated, the spring wires (110) are forced by the inflation to take the shape of the balloon (30). In this way, another means of providing a resecting surface for the balloon (30) is provided by insulating the tips of the spring wires (110) from one another and by providing conductive wire (103) out through the Y junction (40), which can also be used as to provide monopolar or bipolar electrodes for electrocautery.

Figure 6B:
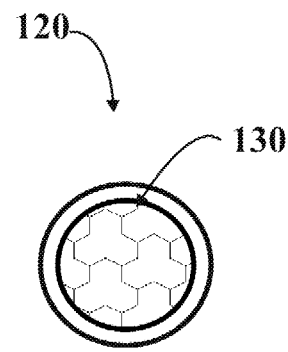
FIG. 6B is an end view of the imaging device of FIG. 6A.
Figure 6A:
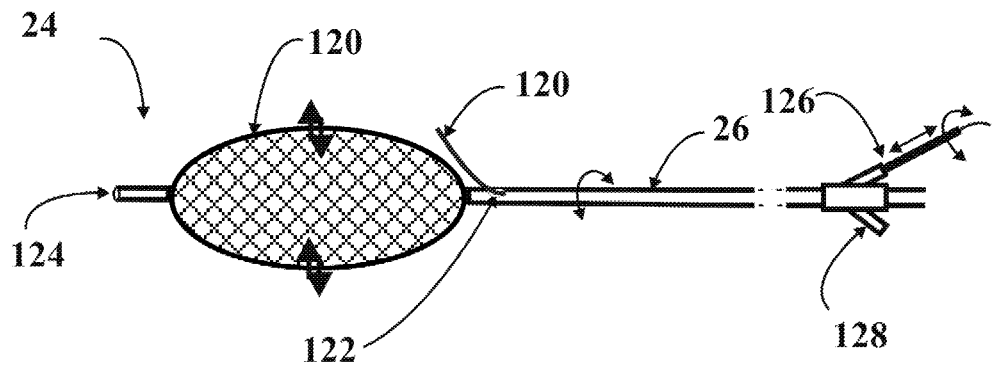
FIG. 6A is a side, partially schematic view of the balloon catheter of FIG. 1 with an imaging device.

In some embodiments, as shown in FIG. 6A, a fiber optic image bundle (120) is introduced through an access hole (122) or (124) to image the surrounding area. At the proximal end of the balloon catheter (26) the Y junction (40) provides access through ports (126) and/or (128). As illustrated in FIG. 6B, the fiber optic image bundle (120) is made of an incoherent fiber bundle (130) for illumination and a coherent imaging fiber bundle (132) at the core, and a lens (not shown). Two separate bundles, one for illumination and the other for image (not shown) can also be used. At the distal end of the fiber optic bundle (120), the imaging coherent fibers are separated from illumination fibers (not shown) and interfaced to an image sensor, such as CMOS or CCD, through appropriate optics (not shown). Similarly, the illumination fibers are interfaced to a light source (not shown). It should be noted, however, that other sources of illumination, such as light emitting diodes, may also be employed. It should also be noted that the image sensor (CCD or CMOS available today in 2 mm size) can be located at the tip of the imaging catheter assembly (not shown), eliminating the need for coherent imaging fiber bundle, thus increasing the image quality and reducing cost.

In this sort of way, the physician can be provided with illuminated light, non-thermal illuminated light, and direct visual feedback of the area ahead of the balloon (30), along the sides of the balloon, and/or behind the balloon. The imaging sensor and illumination optics possess the ability to be translated linearly or rotationally through and/or around the balloon (30), thereby allowing for 360° visualization of the treatment area.

Figure 7A:
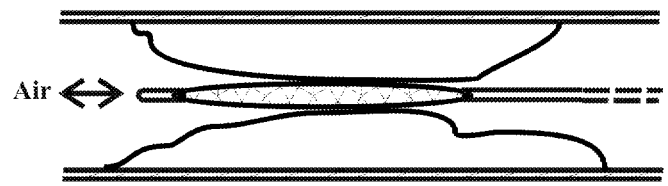
FIGS. 7A-F are side, partially cross-sectional views of the balloon catheter of FIG. 1 being operated in a bodily cavity.

The operation of the balloon (30) can be generally described with reference to FIGS. 7A-F. Referring first to FIG. 7A, after a visual inspection via an endoscope, x-ray, and/or ultrasound, a balloon catheter is selected, and the deflated device is inserted into position in a bodily cavity. This may be accomplished by using the working channel of an endoscope or, as previously noted, along a guide wire that is previously inserted into the body and inserting the proximal end of the guide wire which is outside the body into the inner lumen of the catheter. The catheter is connected to a pump (the components and operation of which are further described in detail below), at which time the pump determines the type of balloon catheter that has been inserted.

Figure 7B:
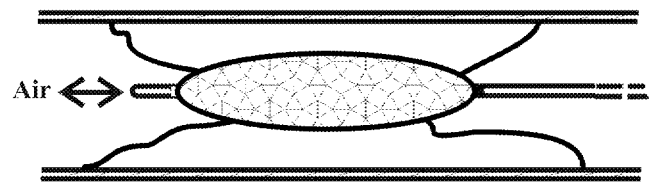

Referring next to FIG. 7B, the balloon is inflated by the pump (which knows the type of balloon to which it is connected) at an air pressure of approximately 2 atmospheres for a fixed amount of time, and the flow is measured (after the physician presses an inflate button on the pump). The pump than calculates the initial approximation of the tissue density and the size of the opening in the tumor tissue, and displays the results for confirmation by the physician. As the pump is operated, this data is continuously updated and displayed.

Figure 7C:
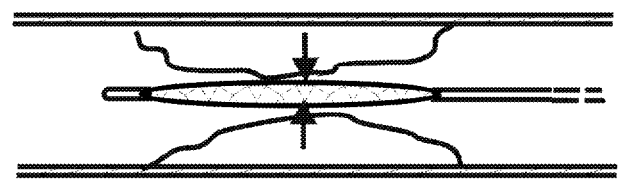
Figure 7D:
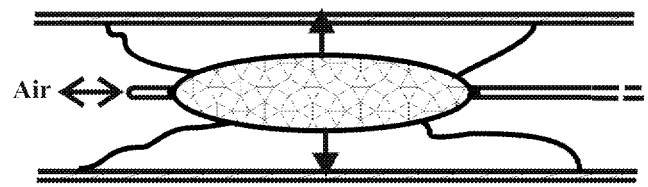

As shown in FIGS. 7C-D, when a pulse button on the pump is pressed, the balloon is deflated and inflated in a cyclical fashion, based either on parameters that were entered by the user, or on default parameters selected by the pump, which are based on the characteristics of the particular balloon (which has been identified as a result of the aforementioned balloon identification plate) and the diameter and/or density measurements made by the system. In this way, the pulse mode of the pump causes the balloon to pulsate according to a desired frequency or change in volume within the balloon, producing a periodically recurring increase and decrease in balloon size.

Accordingly, the resecting surface of the balloon repeatedly comes into contact with the tissue growth, tumor, or other unwanted obstruction to create micro-impacts thereon. As the balloon is deflated and inflated, the resecting surface creates just enough interference fixation, concentrically, along with compressive force excitation and friction upon the unwanted biological material, to promote compressive force exhaustion and abrasion to elicit the decomposition and excision thereof, such that the targeted biological material is resected in a non-traumatic way. As the tissue is destroyed and removed, the balloon is inflated to a larger starting diameter and these steps are repeated until all the unwanted tissue is resected.

Meanwhile, the pump continually monitors the balloon pressure and gas flow, and it updates a graphical display accordingly, as is further described below. This gives the physician an indication as to when to stop the pulse mode and evacuate the loosened tissue.

Figure 7E:
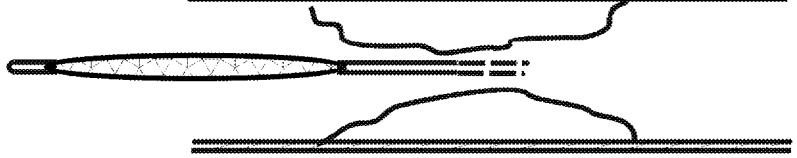

Referring to FIG. 7E, once the tumor and/or tissue is broken up, the balloon is deflated (by pressing a deflate button on the pump), and the balloon is inserted further distally into the bodily cavity, past the location of unwanted tissue.

Figure 7F:
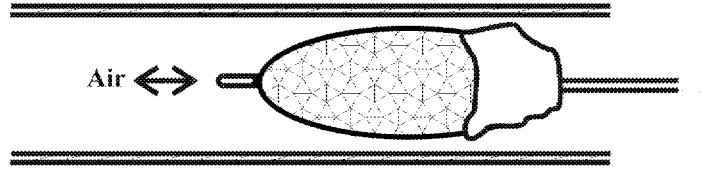

A shown in FIG. 7F, the balloon is then re-inflated (by pressing the inflate button on the pump) and gently pulled towards the proximal end, bringing with it the loose tissue and debris to a point where it can be removed using forceps or suction. In a multi-balloon construct, the debris can be removed through one of the available lumens.

For example, one particular application to optimize 360° lumen des-obstruction, des-occlusion, cleansing, and debris capture involves the use of four bladders in series. All four bladders are first inflated to des-obstruct the lumen. Then, the distal bladder is inflated fully, while the middle distal bladder is deflated completely and the middle proximal bladder is deflated partially. As the balloon catheter is retracted, the middle proximal bladder is optimally inflated, rotation of the middle proximal bladder is initiated, and the debris is thus resected from the inner walls of the lumen. The debris is then captured upon retraction upon the fully inflated distal bladder and contained within the middle distal and proximal bladders.

These steps are repeated as many times as necessary until all of the unwanted tissue is removed. Typically, the procedure will between 5-45 minutes, depending on the density of the tumor or unwanted tissue.

Figure 8:
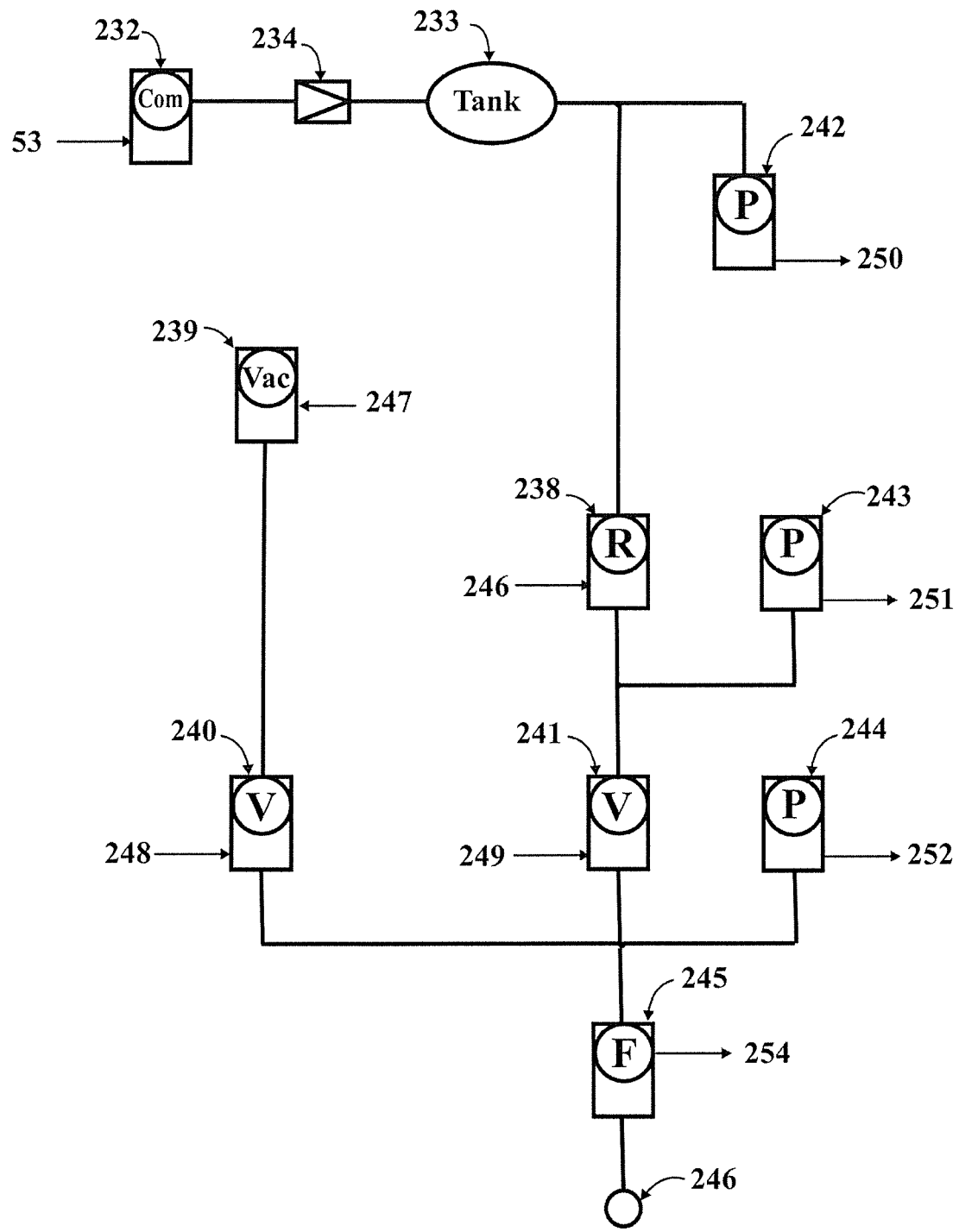
FIG. 8 is a block diagram illustrating the pneumatics of the pump of FIG. 1.

A pump (22) that controls the operation of the resector balloon described above will hereafter be described. FIG. 8 represents a block diagram of the pneumatic components and operation of the pump. The pump includes an air compressor (232) and a pressure tank (233), such as a Festo model CRVZS-0.1, which enable it to achieve up to 10 atmospheres of continuous pressure. The air pressure in the tank (233) is continuously monitored by a microcontroller (254), which is further described in connection with the electronics of the pump (FIG. 9) below. The microcontroller initiates the compressor (232) to operate via an electrical signal output (253) when the tank pressure drops below 4-5 atmospheres. The size of the tank (233) is selected such that at least one procedure can be completed without the compressor operating. The microcontroller calculates and displays the amount of air in the tank (233), which indicates to the user whether there is enough air to complete the procedure. A check valve (234), such as a Festo model H-1/8-A/1, is located between the compressor (232) and the tank (233) in order to prevent the pressured gas from flowing back into the compressor (232). In another variation of the pump (22), however, the above-referenced compressor and pressure tank are not included, and the pressurized air or carbon dioxide is instead provided from an external source, such as gas tank or the operating room walls commonly found in an operating room.

The pressurized gas from the air tank (233) first goes through a pressure regulator (238), which is electronically controlled via an analog electrical output (0V-10V) signal (246) generated by the microcontroller to supply air to the balloon at an exact pressure, which can be set and changed by the physician. However, any pressures higher than the upper limit for the particular balloon being used will generate a warning signal. As explained above, different balloon catheters may be used depending on the application, which are identifiable via key connectors. Therefore, pressure, volume, and flow characteristics of different types of balloons are contained in lookup tables in order to optimize the operation of the balloons and to ensure their consistent performance.

Accordingly, when the pressure is set higher than the balloon's upper limit, the detection of gas flow will cause the pump to stop and produce the warning, and the physician must then take a specific action to override this condition. Similarly, if there is no balloon pressure, the detection of gas flow will also generate a warning, as this may mean the balloon has ruptured. It should further be noted that the pump will also not operate if a catheter is not connected. Additionally, a balloon's operation when first removed from the packaging may vary from its normal operation, requiring that they are first exercised before use in the body. Therefore, the setup and preparation function of the pump allows for this variance.

In certain advantageous embodiments, a vacuum source (239), such as a Festo model VN-05-L-T3-PQ2-VQ2-R01-B, is also included in the pump so that the balloon can be rapidly deflated in a consistent manner. This component also aids in achieving higher frequencies during the pulse mode of operation. The vacuum source (239) is turned on and off by the microcontroller via an electrical output signal (247).

Two microprocessor-controlled solenoid valves—a deflation valve (240) and an inflation valve (241)—are used to control the inflation and deflation of the balloon. The appropriate balloon inflation size is achieved by keeping the gas pressure constant, using the balloon pressure, flow, and volume characteristics from the lookup table data, and timing the on/off activation periods of the valves (240, 241). Deflation valve (240) and inflation valve (241) are controlled by a deflate electrical signal (248) and an inflate electrical signal (249), respectively, which are generated by the aforementioned microcontroller.

The gas pressure is continuously monitored by the microcontroller using pressure regulator (242) at the input from the tank (233), a pressure regulator (243) at the output of the regulator (238), and pressure regulator (244) at the output to the balloon. These pressure regulators, which may be, for example, Festo model SDET-22T-D10-G14-U-M12, provide to the microcontroller analog electrical signal (0V-10V) inputs (250, 251, 252) that vary proportionally to the pressure at the regulators (242, 243, 244). The gas passes through an electronic flow meter (245), such as a Festo model SFET-F010-L-WQ6-B-K1, and a filter (246), before being delivered to the balloon. The flow meter (245) provides an analog electrical signal input (254) to the microcontroller that indicates the amount of gas flow to the balloon.

The pressure regulator (244) and flow meter (245), along with the known dimensions of the balloon, provide the feedback necessary to determine the tumor dimensions and resistance via circumferential force and depth resistance, from which a determination is made as to the diameter of the lumen and the density of the tumor. Using these parameters, the microcontroller makes the appropriate pressure and timing adjustments necessary to maximize the effectiveness of the balloon, provide the physiologic metrics of the affected and non-affected areas, and provide data points and indicators related to the specific dimensional and density characteristics of the intra-lumen anatomy and pathology aid the physician in safely determining and delivering treatment.

In this way, the gas pressure is strictly monitored and maintained at 2 atmospheres in order to keep the balloon from bursting. The high gas input pressure (up to 10 atmospheres) is reduced to and regulated at 2 atmospheres electronically and under software control. However, the pressure delivered to the balloon can be increased or decreased under certain conditions via operator commands.

In some embodiments, one or more temperature sensors are also employed to take continuous physiologic temperature readings of the tissues, tumors, membranes, or other intraluminal tissues and/or devices (whether organic or inorganic) in vivo, before, during, and after the application of cryogenic and/or thermal treatment modalities. In some embodiments, the system takes continuous temperature readings of a cryogenic or thermal treatment device, in vivo, and concurrently assess the temperatures, rates of temperature changes, and depth of energy penetration into the intraluminal tissues to facilitate control of the distribution and/or application of the cryogenic or thermal treatment modality in order to optimize tissue modification and/or dissection.

Figure 9:
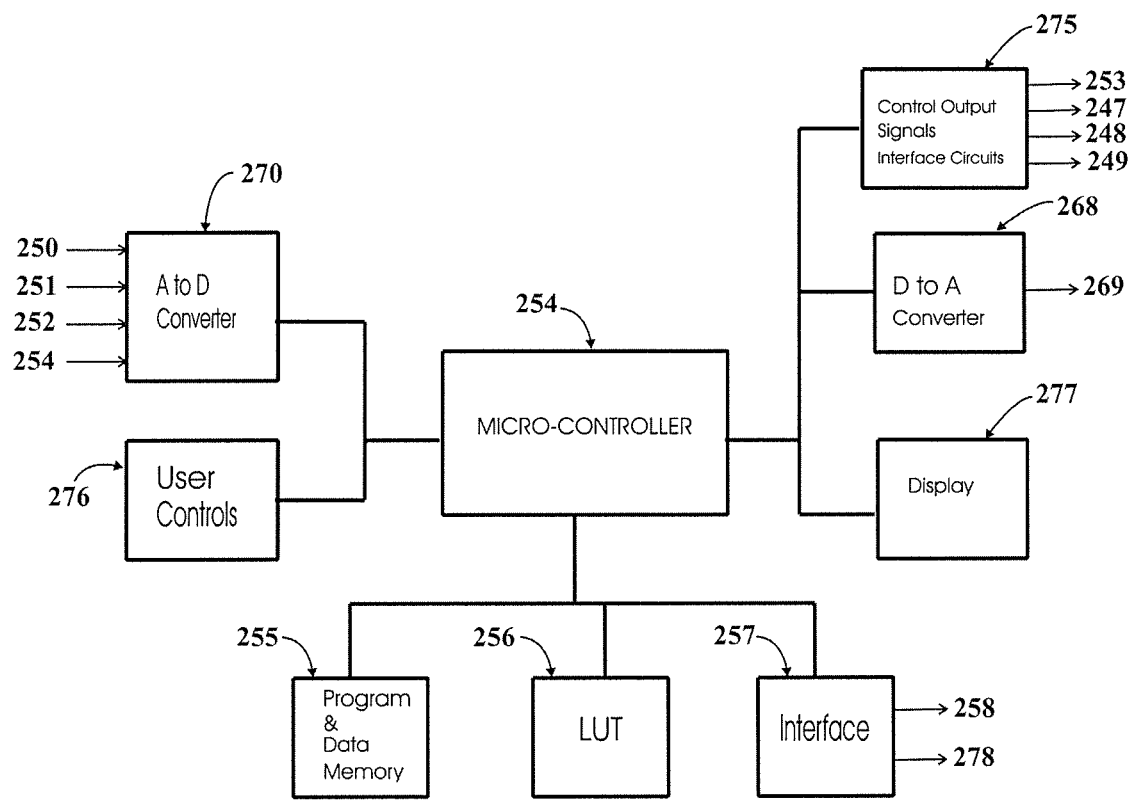
FIG. 9 is a block diagram illustrating the electronics of the pump of FIG. 1.

FIG. 9 represents a block diagram of the components and operation of the electronics of the pump (22). The microcontroller (254) is a RISC processor and lies at the heart of the electronics. Connected to the microcontroller (254) through appropriate electrical signals are the usual static, dynamic, and flash memory (255) for firmware and data, lookup table (256), and an interface (257) for communication with external devices. This interface can be used for programming, updating, diagnostics, and/or control through a Universal Serial Bus (USB) (258). An interface to a remote control hand held unit (278), further described below, can also be established through the interface circuit (257). Additionally, the pump includes a real time date time integrated circuit (not shown).

A digital-to-analog (D to A) converter (268) is used to control the pressure regulator that supplies air pressure to the balloon. The D to A converter (268) generates an analog electrical signal (269) from 0V to 10V that is proportional to the desired pressure. A series of analog-to-digital (A to D) converters (270) allows the microcontroller (254) to read the pressure signal (250) at the pressure air tank (233), the pressure signal (251) at the output of the pressure regulator (238), the pressure signal (252) at the output to the balloon, and the air flow (254) to the balloon.

Another series of digital outputs with appropriate interface circuits (275) allows the microcontroller (254) to control the compressor (232) (ON/OFF) with command signal (253), the vacuum source (239) (ON/OFF) with command signal (247), the deflate solenoid valve (240) (Open/Close) with command signal (248), and the inflate solenoid valve (241) (Open/Close) with command signal (249).

A series of input circuits (276) are connected to switches on the front panel of the pump (22) in order to input user controls, which is further described below. Additionally, a display driver circuit (277) interfaces the microcontroller (254) to the front panel LCD display, also described below.

Figure 10A:
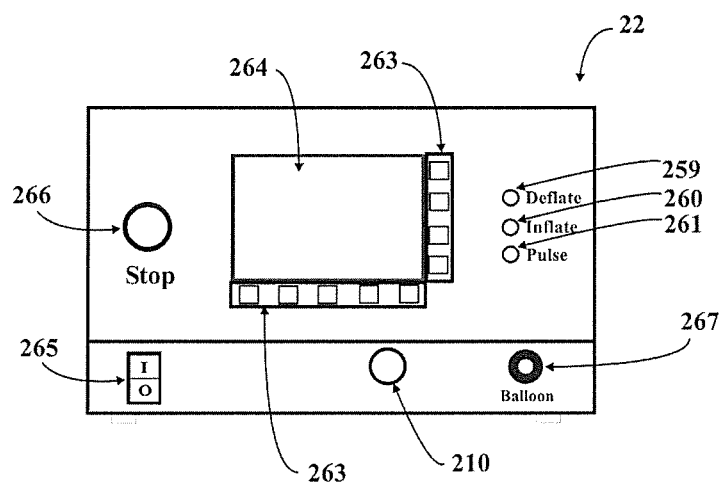
FIG. 10A illustrates a front panel of the pump of FIG. 1.
Figure 10B:
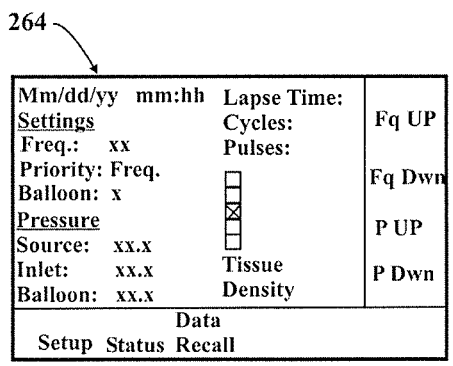
FIG. 10B illustrates a graphical display of the front panel of FIG. 10A.

As shown in FIG. 10A, in certain embodiments, the pump (22) includes user control buttons in the form of soft keys (263) along the bottom and side of a graphical LCD display panel (264). The functions of the control buttons (263) are displayed on the LCD panel (264) and change depending on the mode of the pump. The buttons (263) can be used to enter a setup mode, display settings, recall collected data, or increase/decrease frequency and pressure. In addition to the soft key functions, the graphical LCD display (264) may show the pump's settings, pressure, frequency, and flow values, warnings, other information such as time, date, and elapsed time, and any other information that may be useful to the physician for conducting the procedure and for gathering procedural data, as shown in FIG. 10B.

The front panel of the pump (22) includes a deflate button (259), an inflate button (260), and a pulse button (261) to change the mode in which the pump (22) is operating. The front panel also includes an On/Off switch (265), as well as an emergency stop button (266), which stops the airflow to the balloon by closing the inflate valve (241) and opening the deflate valve (240) and starting the vacuum source (239). Also included on the front panel of the pump (22) is one or more keyed receptacle(s) (267) for the aforementioned keyed connector(s) of the balloon catheter.

Figure 10C:
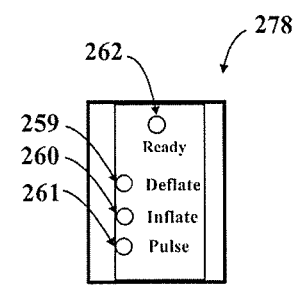
FIG. 10C illustrates a front panel of a remote for the pump of FIG. 10A.

In certain embodiments, the front panel of the pump (22) also includes an interface (210) for a handheld remote control (278), as previously described. This handheld remote control (278), shown in FIG. 10C, can be located in the sterile field, and can be hardwired or wirelessly connected to the pump (22) using readily available communication technologies, such as infrared or radio frequency (i.e. Bluetooth). Just like the front panel of the pump (22), the remote control (278) has three push buttons (259, 260, 261) for deflation, inflation, and pulse commands. The remote control (278) also has a ready light (262) that indicates when it is ready to accept a command.

Figure 11A:
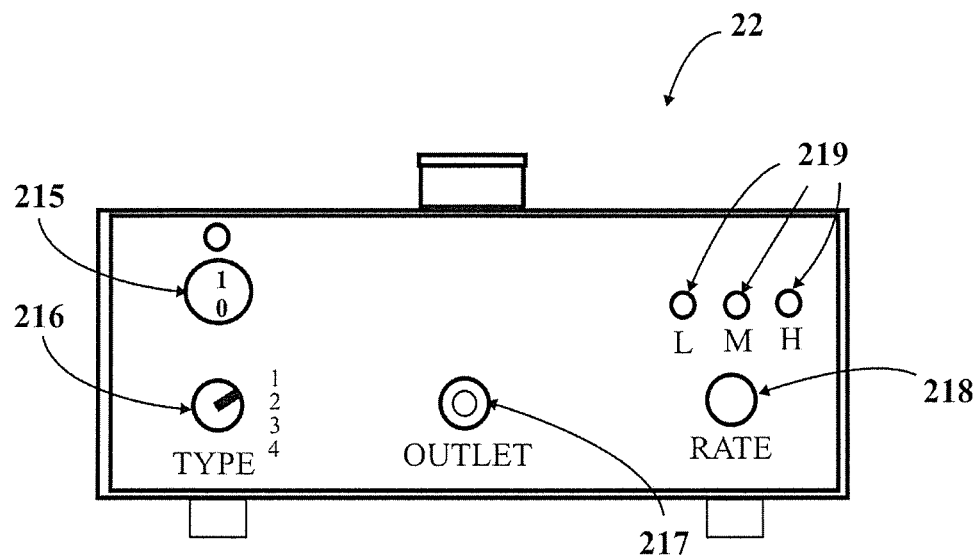
FIG. 11A illustrates a front panel of the pump of FIG. 1.
Figure 11B:
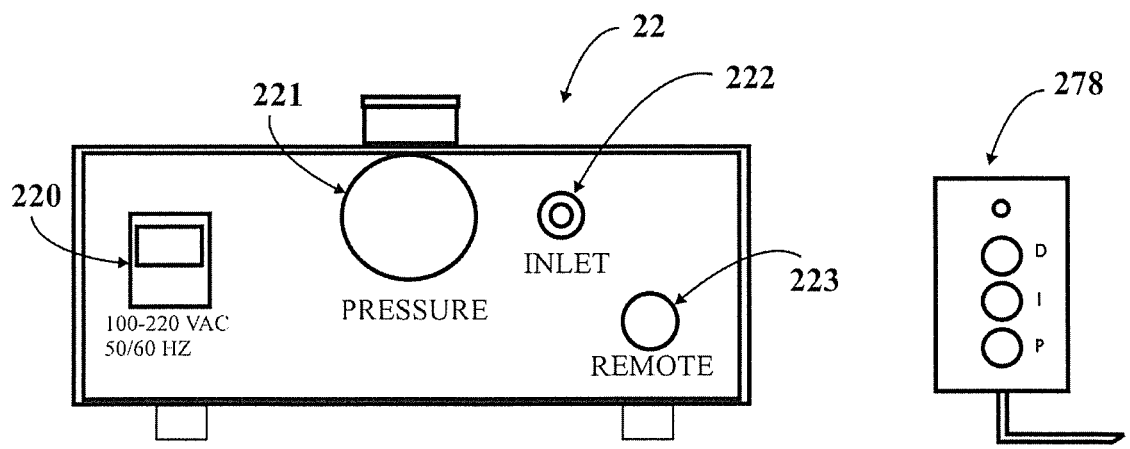
FIG. 11B illustrates a rear panel of the pump of FIG. 11A.
Figure 11C:
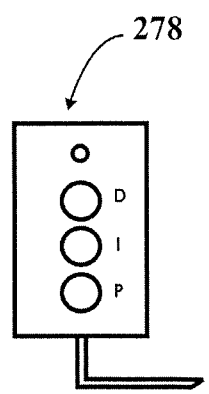
FIG. 11C illustrates a front panel of a remote for the pump of FIG. 11A.

As shown in FIG. 11A-C, in another variation of the pump (22), the compressor, the pressurized air tank, and the vacuum source are not included. Even though the balloon could deflate faster with a vacuum source, the elasticity of the fiber mesh and latex balloon will still generate sufficient frequency to make it useful. As shown in FIG. 11A, the front panel of the device includes a pump On/Off switch (215), a balloon TYPE selector knob (216), a balloon OUTLET connector (217), a balloon inflation/deflation RATE selection push button switch (218), and rate L (low), M (medium), and H (high) indicator LEDs (219). As shown in FIG. 11B, the rear panel includes a VAC power inlet (220), PRESSURE control knob (221), pressurized gas INLET connector (222) and REMOTE control connector (223). The balloon pressure gauge is located on top of the unit.

Figure 12A:
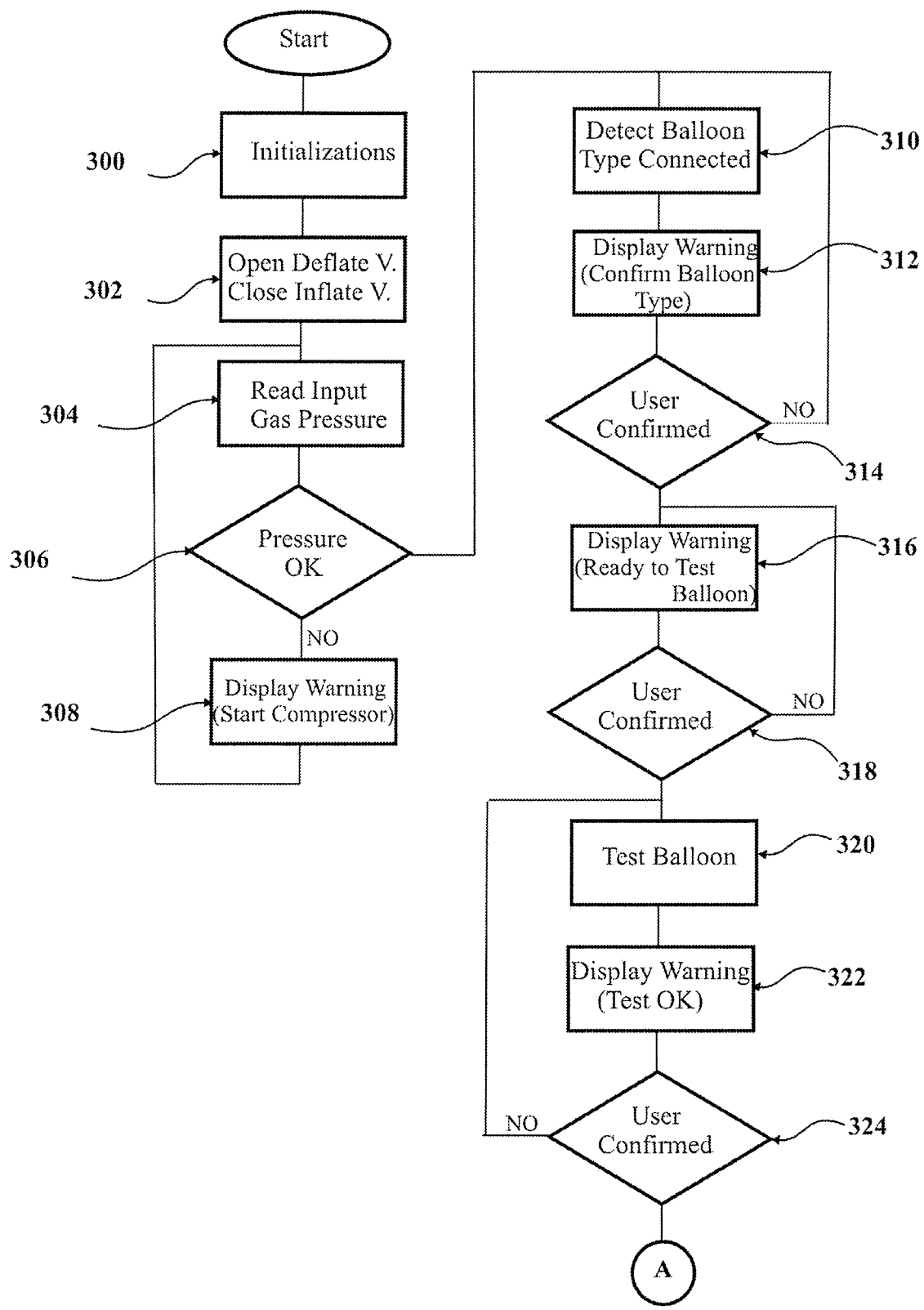
FIGS. 12A-B is a flow diagram illustrating the operation of the resector balloon system of FIG. 1.
Figure 12B:
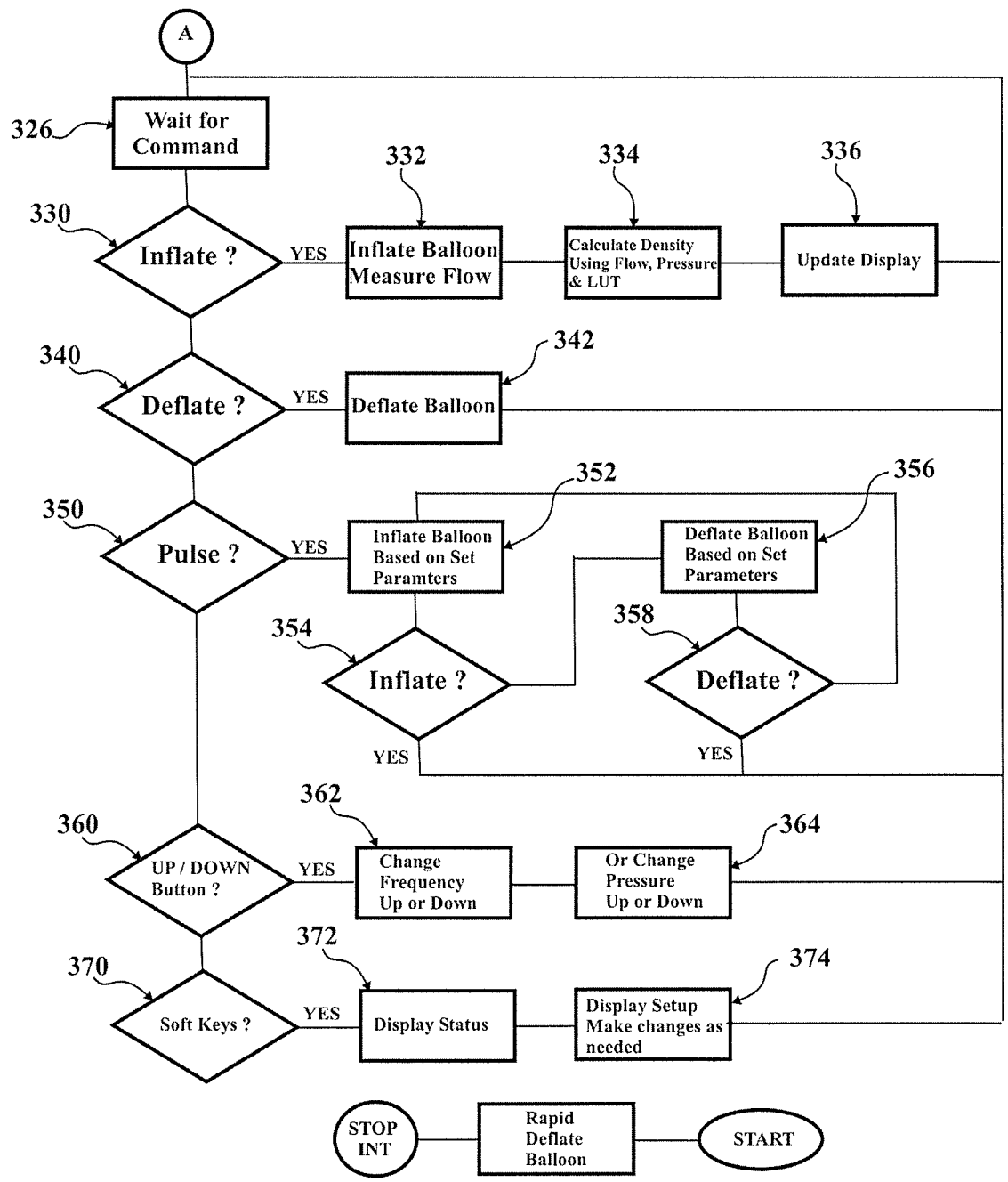

The operation of the system will now be described with reference to FIGS. 12A-B. An initialization step includes setting up and running diagnostic testing on all internal components, including pressure transducers, flow meters, solenoid valves, etc., and displaying any warnings or, if no problems are detected, displaying a system READY indication to the user (step 300).

After initialization, the pump opens the deflate valve and closes the inflate valve to insure that there is no air pressure and flow at the outlet to the balloon catheter (step 302). The system will then read the internal tank pressure (step 304). If the pressure is too low (decision block 306), the system will display the amount of air available and wait for user confirmation to start the compressor (step 308). Alternatively, if an internal compressor is not available, the air pressure at the inlet will be read and a warning will be displayed to connect external pressured air.

The system will then display a message and wait for a balloon catheter to be connected. When the balloon is connected, it will be detected through electro-optical or electro-mechanical means (step 310) and display a message to the user to confirm the balloon type (step 312). If confirmed with the user (decision block 314), the system will then display a message to the user to confirm that the balloon should be tested (step 316) and, if confirmed by the user (decision block 318), the balloon will be tested and pre-exercised (step 320). The system will then display a message to the user (step 322), and upon receiving confirmation from the user (decision block 324), will scan for a command from the front panel, the remote control, or a serial interface (step 326). During the operation of the system and while waiting for a command, receipt of the emergency stop command will cause the rapid deflation of the balloon.

Each "inflate" command (command 330) will inflate the balloon by an incremental amount based on the type of balloon that is connected (step 332). This incremental inflation is accomplished by opening the inflate valve for a set amount of time while the deflate valve remains closed. In this way, the balloon is inflated to the size desired by the user. Alternatively, pressing and holding the inflate button will inflate the balloon in a continuous fashion.

Figure 13:
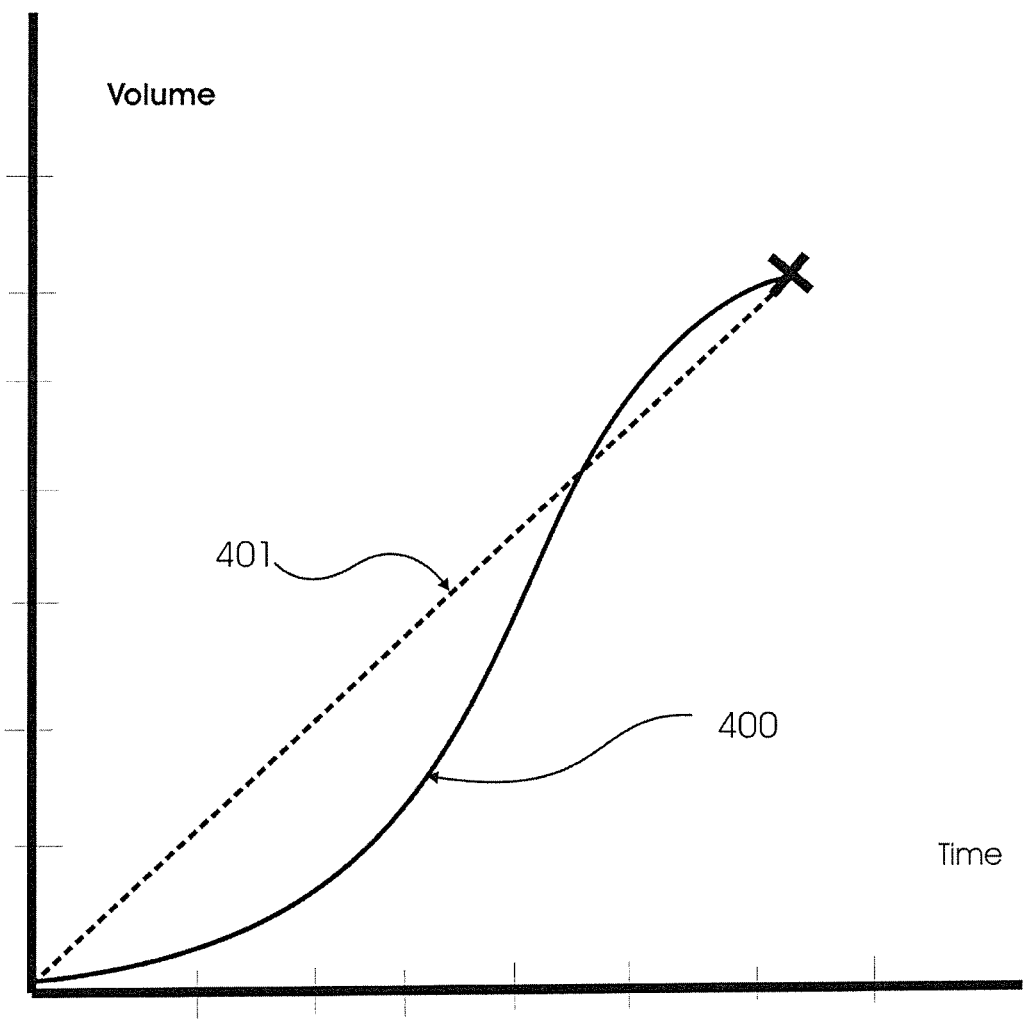
FIG. 13 is an example of a typical plot of volume versus flow time characteristics before and after correction.

While inflating, the flow of gas (ml/sec) is measured (step 332). After closing the inflate valve, the balloon pressure is measured, and an approximation of the volume V is made based on the ideal gas law (V=nRT/P) and the lookup table, which contains balloon characteristics and universal constants (step 334). Here, T is assumed constant at 310°K (body temperature can be measured and entered into the equation as well), R is a gas law constant, n is moles of gas, which is proportional to the measured flow, and P is the measured pressure. With each incremental inflation, V is recalculated, and the relative volume change (V2−V1) is displayed (step 336). Knowing the shape of the balloon from the balloon identification, and using the data from the lookup table, the relative change in balloon diameter (D2−D1) is also calculated and displayed. As shown in FIG. 13, typical volume versus flow time characteristic data can be depicted in a graphical format. A typical characteristic performance curve of the balloon (400) is translated to an actual linear performance (401).

Similarly, each "deflate" command (command 340) incrementally deflates the balloon by opening the deflate valve for set period of time while the inflate valve remains closed (step 342).

When the pump receives a "pulse" command (command 350), the balloon is inflated and deflated in a pulsed fashion based on set parameters (step 352, decision block 354, step 356, decision block 358), which include an inflation priority. In the pulse mode, this aspect of the inflate/deflate cycles can be set as desired. The pump has a feature to control this function based on change in volume (delta volume) or frequency priority. Because the gas pressure is maintained at a constant value (i.e., 2 atmospheres), the time it will take to inflate the balloon to the desired size will vary due to the different sizes and volumes of the types of balloons. Therefore, in the delta volume priority, the maximum and minimum frequencies are calculated and set for the particular balloon used in order to maximize the delta volume between the inflated and the deflated states. In the frequency priority, the maximum and minimum delta volumes are calculated and set for the particular balloon in order to maximize the frequency of the inflate/deflate cycles.

Delta volume and/or frequency is calculated for each inflation/deflation cycle, and the display is updated accordingly. If the "Inflate" button is pressed during this pulse mode, the pulse mode is stopped with the balloon in the inflated state. Likewise, if the "Deflate" button is pressed during the pulse mode, the pulse mode stops with the balloon in the deflated state.

If the user wishes to change the set frequency and/or delta volume for the pulse mode, this can be done by pressing the Up/Down soft keys located on the LCD display panel (command 360, steps 362-364). The user can also press soft keys located on the display panel to enter the status and setup displays (command 370, steps 372-374). These include screens to set up and enter initialization data into the system, and to displaying data accumulated during the procedure.

It should be noted that, during all states of operation of the pump, the vacuum source is turned on and off to achieve faster deflation and higher inflation/deflation cycles.

It should be noted that, while the described embodiments have at times been described with respect to use on tumors and tissue, the system may also be employed in other applications. Similarly, while the present invention has been described with respect to the pulsation mechanism of action described herein, such action is not exclusive. That is, other mechanisms of action may be employed in addition to pulsation as needed, such as linear translation of the balloon along the catheter, as well as rotation. Such motion may be particular useful in cases, such as, for example, plaque excision and mucosa resection in ENT applications.

Another example in which the above-described system can be usefully employed is to remedy the decompression of compressed articulations in restoring articular joint spaces, heights, and functions in a minimally invasive fashion. The decompression balloon includes a wide variety of shapes and dimensions to address and replicate the broad anatomic joint dimensions found in human and other mammalian bodies, including the spine, knee, shoulder, hip, ankle, elbow, wrist, hands, fingers, feet, toes jaw, ribs, clavicle, and related articulations. An application of this art would be as a minimally invasive method to deploy an interspinous process spacer comprised of a unique geometric, dimensional balloon construct that possessed the ability, when inflated, to decompress the interspinous process articulation. The balloon construct could be inserted under endoscopic, radiographic, and/or ultrasound visualization via a small incision and/or via wire guidance. Then, the balloon spacer would be inflated to provide the requisite decompression of the interspinous process. As a result, the stress shielding and failure modalities often witnessed using current materials and methods can be mitigated. This method is widely applicable to the many articular joints in the human and mammalian bodies.

The above-described system can be used for minimally invasive interventional treatment for Facet Joint fusion. A unique dimensionally shaped balloon that mimics the articular surfaces of the facet joint is deployed to the facet joint via wire guidance under endoscopic and/or fluoroscopic visualization and then inflated. The abrasive mesh-like surface of the balloon is concentrically and radially pulsed to create micro-abrasions upon the articular cartilage, and ablative energy is then applied to the conductive ridges atop the exterior surface of the balloon, eliciting decomposition and decortication of the articular surface. Any bleeding is tamponaded by inflating the balloon to create compression and/or via application of electrosurgical energy that is transmitted via the conductive ridges atop the exterior surface of the balloon. The balloon is then rotated to further decorticate and widen the articular space. The balloon is then deflated, and an inert implant, bone dowel, or other osteo-conductive and osteo-promotive biologic implant is then inserted along the deflated catheter and/or guide wire and into the articular joint space to create an interference fit and promote fusion. An iteration of this procedure would also include the deployment of a facet joint replacement implant. This procedure has broad application across the broad spectrum of articular joint fusion and articular joint replacement.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A system for controlling a supply of fluid to a balloon attached to a catheter, said system comprising:
   a pump having a connector for connecting to the catheter, said pump including:
   a processor; and
   at least one sensor for making at least one measurement;
   said pump configured to receive balloon profile data identifying the type of balloon attached to the catheter; and
   said pump configured to control the supply of fluid to the balloon based at least partially on the type of balloon and the at least one measurement.

2. The system of claim 1, wherein said connector is an identification connector with which said pump identifies the balloon type.

3. The system of claim 2, wherein said identification connector comprises:
   a balloon identification plate; and
   a key that orients said identification plate when said catheter is connected to said pump such that said pump identifies said balloon type using said identification plate.

4. The system of claim 3 wherein said balloon identification plate utilizes an electro-optic identification scheme.

5. The system of claim 3, wherein said balloon identification plate utilizes an electro-mechanical identification scheme.

6. The system of claim 1, wherein said at least one sensor comprises a sensor that is configured to determine a pressure of the fluid output to the balloon and a sensor that determines the flow of the fluid output to the balloon.

7. The system of claim 1, wherein said processor is configured to calculate a diameter in a biological cavity based at least partially on the at least one measurement.

8. The system of claim 1, wherein said processor is configured to determine an inflation frequency of, or change in volume in, the balloon based at least partially on the balloon profile data.

9. The system of claim 8, wherein said pump is configured to control the supply of fluid to the balloon based at least partially on the determined inflation frequency or change in volume.

10. The system of claim 1, wherein said pump further comprises a vacuum source.

11. The system of claim 10, wherein said vacuum source is configured to evacuate resected material via a channel in the catheter or evacuate fluid from the balloon.

12. The system of claim 1, wherein said processor is configured to control an inflation frequency of, or a change in volume in, the balloon.

13. The system of claim 12, wherein said processor is configured to receive a frequency selection or a change in volume selection based on a user input to an interface.

14. The system of claim 1, further comprising a deflation valve and an inflation valve, wherein said processor is configured to control said deflation valve and said inflation valve to control inflation and deflation of the balloon.

15. The system of claim 1, wherein the balloon profile data is stored in a look up table and upon identification of the connected balloon, said processor is configured to gather the balloon profile data corresponding to the identified balloon type.

16. The system of claim 1, wherein said pump is configured to receive the balloon profile data via a user input to an interface.

17. The system of claim 1, wherein said processor is configured to calculate a density of a tumor in a biological cavity based at least partially on the at least one measurement.

18. The system of claim 1, wherein said pump further includes:
an air tank;
a compressor for pressurizing and supplying air to the tank; and
a pressure regulator through which the fluid is supplied from the air tank to the balloon, wherein the pressure regulator supplies the fluid to the balloon at a particular pressure based on a signal generated by the processor.

19. The system of claim 18, wherein said pump further includes a flow meter through which the fluid is supplied from the regulator to the balloon.

20. The system of claim 19, wherein:
said pump further includes an additional pressure regulator at the output of the flow meter to the balloon; and
the pump makes at least one measurement based at least partially on feedback from the flow meter and the additional pressure regulator.

* * * * *